US009279809B2

(12) United States Patent
Tateno et al.

(10) Patent No.: US 9,279,809 B2
(45) Date of Patent: ＊Mar. 8, 2016

(54) CELL DIFFERENTIATION ASSAY METHOD, CELL ISOLATION METHOD, METHOD FOR PRODUCING INDUCED PLURIPOTENT STEM CELLS, AND METHOD FOR PRODUCING DIFFERENTIATED CELLS

(71) Applicants: National Institute of Advanced Industrial Science and Technology, Tokyo (JP); Wako Pure Chemical Industries, Ltd., Osaka (JP)

(72) Inventors: Hiroaki Tateno, Ibaraki (JP); Jun Hirabayashi, Ibaraki (JP); Makoto Asashima, Ibaraki (JP); Yuzuru Ito, Ibaraki (JP); Yasuko Onuma, Ibaraki (JP); Masaki Warashina, Hyogo (JP); Masakazu Fukuda, Hyogo (JP)

(73) Assignees: NATIONAL INSTITUTE OF ADVANCED INDUSTRIAL SCIENCE AND TECHNOLOGY, Tokyo (JP); WAKO PURE CHEMICAL INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/381,116

(22) PCT Filed: Feb. 27, 2013

(86) PCT No.: PCT/JP2013/001160
§ 371 (c)(1),
(2) Date: Aug. 26, 2014

(87) PCT Pub. No.: WO2013/128914
PCT Pub. Date: Sep. 6, 2013

(65) Prior Publication Data
US 2015/0111218 A1 Apr. 23, 2015

(30) Foreign Application Priority Data

Feb. 28, 2012 (JP) .................................. 2012-041418
Dec. 6, 2012 (JP) .................................. 2012-267679

(51) Int. Cl.
*G01N 33/569* (2006.01)
(52) U.S. Cl.
CPC .............................. *G01N 33/56966* (2013.01)
(58) Field of Classification Search
None
See application file for complete search history.

(56) References Cited

FOREIGN PATENT DOCUMENTS

EP 2774994 A1 9/2014
JP 2011-149826 8/2011
WO 2008087258 A1 7/2008
WO 2010/131641 11/2010

OTHER PUBLICATIONS

Tateno, et al., Glycome Diagnosis of Human Induced Pluripotent Stems Cells Using Lectin Microarray; Journal of Biological Chemistry, Jun. 10, 2011, 286(23):20345-20353; The American Society for Biochemistry and Molecular Biology, Inc., USA.
Wang, et al., Specific lectin biomarkers for isolation of human pluripotent stem cells identified through array-based glycomic analysis, Cell Research, Sep. 6, 2011, 21:1551-1563.
Toyoda, et al., Lectin microarray analysis of pluriopotent and multipotent stem cells,Genes to Cells, 2011, 16:1-11, The Molecular Biology Society of Japan/Blackwell Publishing Ltd.
Hamanoue, et al., Cell surface N-glycans mediated isolation of mouse neural stem cells, Journal of Neurochemistry, 2009, 110:1575-1584, International Society for Neurochemistry.
Sulak, et al., A TNF-like Trimeric Lectin Domain from Burkholderia cenocepacia with Specificity for Fucosylated Human Histo-Blood Group Antigens, Structure, Jan. 13, 2010, 18:59-72, Elsevier Ltd.
Tang, et al., An antibody against SSEA-5 glycan on human pluripotent stem cells enables removal of teratoma-forming cells; Nature Biotechnology, Sep. 2011, 29(9):829-834 and "Online Methods"page.
International Stem Cell Initiative (Adewumi, et al.), Characterization of human embryonic stem cell lines by the International Stem Cell Initiative, Nature Biotechnology, Jul. 2007, 25(7):803-816.
Iijima, et al., Position-Specific Incorporation of Fluorescent Non-natural Amino Acids into Maltose-Binding Protein for Detection of Ligand Binding by FRET and Fluorescence Quenching, ChemBioChem, 2009, 10:999-1006, Wiley-VCH.
Suemori, et al., Efficient establishment of human embryonic stem cell lines and long-term maintenance with stable karyotype by enzymatic bulk passage, Biochemical and Biophysical Research Communications, 2006, 345:926-932, Elsevier Inc.
Draper, et al., Surface antigens of human embryonic stem cells: changes upon differentiation in culture, J. Anat., 2002, 200:249-258, Anatomical Society of Great Britain and Ireland.

(Continued)

*Primary Examiner* — Jacob Cheu
(74) *Attorney, Agent, or Firm* — Pearne & Gordon LLP

(57) ABSTRACT

Provided are a method for accurately evaluating the differentiation status of stem cells by selectively staining only stem cells in an undifferentiated state, and a method for positively isolating only stem cells in an undifferentiated state. Specifically provided is a method for determining differentiation of a cell comprising a step of contacting a test cell with a probe comprising protein (A) or (B) below and a step of detecting the presence of binding of the probe to the test cell. The method for determining differentiation of a cell is capable of detecting the presence or absence of an undifferentiated stem cell in test cells by using a probe that specifically reacts with undifferentiated stem cells and detecting the presence of bonding to the test cell. (A) A protein comprising an amino acid sequence shown in SEQ ID NO: 1 and recognizing a sugar chain structure of "Fucα1-2Galβ1-3GlcNAc" and/or "Fucα1-2Galβ1-3GalNAc;" and (B) a protein comprising an amino acid sequence showing 80% or more similarity to the amino acid sequence shown in SEQ ID NO: 1 and recognizing a sugar chain structure of "Fucα1-2Galβ1-3GlcNAc" and/or "Fucα1-2Galβ1-3GalNAc."

20 Claims, 13 Drawing Sheets

(56) References Cited

OTHER PUBLICATIONS

Takahashi, et al., Induction of Pluripotent Stem Cells from Adult Human Firbroblasts by Defined Factors, Cell, Nov. 30, 2007, 131:861-872, Elsevier, Inc.

International Search Report of PCT/JP2013/001160, May 14, 2013, pp. 1-6.

Onuma, et al., rBC2LCN, a new probe for live cell imaging of human pluripotent stem cells; Biochemical and Biophysical Communications, 2013, vol. 431, pp. 524-529.

Communication and extended European Search Report issued in corresponding European Patent Application No. 13755221.2; Dated Nov. 6, 2015.

CELL DIFFERENTIATION ASSAY METHOD, CELL ISOLATION METHOD, METHOD FOR PRODUCING INDUCED PLURIPOTENT STEM CELLS, AND METHOD FOR PRODUCING DIFFERENTIATED CELLS

TECHNICAL FIELD

The present invention relates to a method for determining differentiation of a cell, a cell separation method, a method for producing induced pluripotent stem cells, and a method for producing differentiated cells. More specifically, the present invention relates to a method for determining the differentiation status of test cells by using a protein recognizing a sugar chain structure specific for undifferentiated cells, and the like.

BACKGROUND ART

Pluripotent stem cells have attracted attention because of having the property of being capable of differentiating into various cells constituting the body and the property of being capable of maintaining their characteristics being undifferentiated, and are not only applied to drug discovery screening and elucidation of disease mechanisms but also under worldwide study as a material for regenerative medicine.

The world's first phase 1 clinical trial using human ES cells started against acute spinal-cord injury in the U.S.A in 2010; furthermore, an investigational new drug (IND) application for phase ½ clinical trials using human ES cells against retinal degenerative disease was approved by FDA; and regenerative medicine research using human pluripotent stem cells continues rapid development.

Particularly, iPS cells as new human pluripotent stem cells originating in Japan have great advantage that they have a low ethical roadblock because of, for example, no use of fertilized embryos and can be established also from autologous tissue, and thus they are receiving high expectations from the field of regenerative medicine. In Japan, Riken Center for Developmental Biology, Institute of Biomedical Research and Innovation Laboratory, and other institutes plan to start clinical studies using iPS cells with age-related macular degeneration patients in fiscal 2013, and Keio University also intends to start clinical studies in spinal cord injury patients in 2015.

As the clinical application of human pluripotent stem cells such as ES cells and iPS cells are started as just described above, a system to supply cells by securing quality and safety is not sufficiently developed. For pluripotent stem cells, the preparation method, culture conditions, storage conditions, and the like affect qualities such as characteristics being undifferentiated, differentiation potency, and proliferative capacity. Thus, managements not based on an appropriate method may produce results different for each producer and each user. This becomes a cause of bringing negative effects such as the decreased reliability of stem cell therapy and the occurrence of health hazards due to the therapy. Thus, there are necessary a maintenance culture method high in reliability and reproducibility and a measurement/evaluation system.

For example, although pluripotent stem cells are not directly used but used after differentiating them into desired cells for transplantation in a cell therapy, it has been pointed out that if a cell source having differentiated into desired cells is contaminated with undifferentiated cells, these undifferentiated stem cells become a cause of tumorgenesis. Accordingly, there is a need for the development of a technique for evaluating whether cells to be used for cell therapy are contaminated with undifferentiated stem cells, i.e., tumorgenic cells.

In contrast, somatic stem cells, which are various compared to human pluripotent stem cells including ES cells and iPS cells, have been in clinical application as established techniques. However, it is not easy to stably obtain cells having quality suitable for transplantation; thus, it represents a very important challenge to establish a quality verification method for somatic stem cells and a stable culture method based thereon. There is also a need for the development of a quality verification method for cells before transplantation in evaluating the effectiveness of cell transplantation using somatic stem cells, understanding the mechanism thereof, and evaluating risk.

Previously, the present inventors exhaustively analyzed the sugar chain profiles of human iPS cells (114 specimen) prepared from 5 types of different somatic cells (skin, fetal lung, endometrial membrane, placental artery, and amniotic membrane) and human ES cells (9 specimen), using lectin microarray.

As a result, despite the different sugar chain profiles of the original somatic cells for each tissue, it was found that all of the prepared iPS cells showed almost the same sugar chain profile and the introduction of reprogramming genes caused uniform convergence into sugar chain structures analogous to those of ES cells. According to the results of analyzing the lectin array data of human ES/iPS cells and human somatic cells in detail, the expression level of α2-6Sia, al-2Fuc, and type 1 LacNAc was presumed to be markedly increased in undifferentiated human ES/iPS cells compared to in somatic cells. In addition, the presumption was confirmed by a method using expression analysis of glycosyltransferase genes using DNA array (Non Patent Literature 1).

The BC2LCN lectin is a BC2LCN lectin (YP_002232818) that corresponds to the N-terminal domain of the BC2L-C protein derived from a gram-negative bacterium (*Burkholderia cenocepacia*), and is a lectin recognizing the sugar "Fucα1-2Galβ1-3GlcNAc" and "Fucα1-2Galβ1-3GlcNAc" in the nonreducing terminus of a complex sugar chain (Non Patent Literature 3). The present inventors succeeded in obtaining BC2LCN lectin as a recombinant (hereinafter sometimes described as "rBC2LCN") expressed in transformed *Escherichia coli* (Non Patent Literature 1).

In the above-described experiment using the lectin array, the present inventors found that rBC2LCN lectin reacted with all human ES/iPS cells but completely failed to react with differentiated somatic cells (skin, fetal lung, endometrial membrane, placental artery, and amniotic membrane). It is construed that BC2LCN lectin specifically reacts with the sugar chain structures "Fucα1-2Galβ1-3GlcNAc (=H type 1 structure)" and "Fucα1-2Galβ1-3GalNAc (=H type 3 structure)" having 2 (al-2Fuc and type1 LacNAc) of "al-2Fuc", "type1 LacNAc", and "α2-6Sia". These two sugar chain structures are sugar chains highly expressed on human ES/iPS cells and hardly expressed on differentiated cells of the skin, fetal lung, endometrial membrane, placental artery, and amniotic membrane.

This indicates that the sugar chain ligand recognized by BC2LCN lectin is a novel undifferentiation sugar chain marker characterizing undifferentiated cells and also indicates that BC2LCN lectin can be used as a probe specific for the undifferentiation sugar chain markers "Fucα1-2Galβ1-3GlcNAc" and/or "Fucα1-2Galβ1-3GalNAc" (hereinafter, both are sometimes together referred to as "Fucα1-2Galβ1-3GlcNAc/GalNAc").

Thereafter, the team of Drukker et al. also found that an antibody recognizing "Fucα1-2Galβ1-3GlcNAc" recognizes ES and iPS cells in an undifferentiated state (Non Patent Literature 2), supporting the above findings of the present inventors.

However, the antibody of Drukker et al. specifically reacts with "Fucα1-2Galβ1-3GlcNAc (=H type 1 structure)" but does not react with "Fucα1-2Galβ1-3GalNAc (=H type 3 structure)". This predicts that the antibody falls short of the rBC2LCN lectin of the present inventors from the viewpoint of discrimination when used to detect the undifferentiated stem cell markers because the antibody cannot detect "Fucα1-2Galβ1-3GalNAc" or "Fucα1-2Galβ1-3GalNAc-containing sugar chain" in undifferentiated stem cells as compared to the rBC2LCN lectin of the present inventors.

CITATION LIST

Non Patent Literature

Non Patent Literature 1: Tateno H, Toyota M, Saito S, Onuma Y, Ito Y, Hiemori K, Fukumura M, Matsushima A, Nakanishi M, Ohnuma K, Akutsu H, Umezawa A, Horimoto K, Hirabayashi J, Asashima M., J. Biol. Chem. 2011 Jun. 10; 286 (23): 20345-53.
Non Patent Literature 2: Tang C, Lee A S, Volkmer J P, Sahoo D, Nag D, Mosley A R, Inlay M A, Ardehali R, Chavez S L, Pera R R, Behr B, Wu J C, Weissman I L, Drukker M., Nat. Biotechnol. 2011 Aug. 14; 29 (9): 829-34.
Non Patent Literature 3: Sulak O, Cioci G, Delia M, Lahmann M, Varrot A, Imberty A, Wimmerova M., Structure. 2010 Jan. 13; 18 (1): 59-72.
Non Patent Literature 4: International Stem Cell Initiative. Characterization of human embryonic stem cell lines by the International Stem Cell Initiative. Nat. Biotechnol. 2007 July; 25 (7): 803-16.
Non Patent Literature 5: Iijima et al. (2009) Chem. Bio. Chem., 10, 999-1006.
Non Patent Literature 6: Suemori H, Yasuchika K, Hasegawa K, Fujioka T, Tsuneyoshi N, Nakatsuji N. (2006) Biochem. Biophys. Res. Commun. 345, 926-932.
Non Patent Literature 7: Draper J S, Pigott C, Thomson J A, Andrews P W. (2000) J. Anat. 200, 249-58.
Non Patent Literature 8: Takahashi K., Tanabe K., Ohnuki M., Narita M., Ichisaka T., Tomoda K., Yamanaka S. (2007) Cell 131, 861-872.

SUMMARY OF INVENTION

Technical Problem

Currently, when the quality of cells is inspected, it is common to analyze the difference in the gene expression of cells, the epigenomic state, the cell surface marker, or the like using a means such as a sequencer, microarray, flow cytometry, or immunohistochemistry. Among these methods, the most common method for determining the state of a cell is a method involves staining a cell surface marker with a molecular probe such as an antibody using flow cytometry or an immunohistochemical technique. To perform these methods, it is necessary for a molecule providing a marker for a desired cell and a molecule specifically binding thereto to be present. Hence, there has been a need for a molecule capable of more clearly discriminating the states of cells and preferably present on the cell surface.

An object of the present invention is to provide a method for accurately evaluating the differentiation status of stem cells and a method for positively isolating only stem cells in an undifferentiated state or only differentiated cells.

Solution to Problem

As described above, the present inventors were successful in ascertaining sugar chain structures providing undifferentiation sugar chain markers distinguishing between undifferentiated stem cells and differentiated cells, and identified BC2LCN lectin accurately distinguishing between the markers for undifferentiated stem cells.

However, an evanescent wave excited fluorescence method as developed by the present inventors has been used mainly as a method for detecting a sugar chain by a lectin because the lectin is generally low in specificity and affinity for a ligand compared to an antibody or the like. Specifically, the method is a method involving fluorescently labeling a cell extract in which test cells are ground, reacting the fluorescence-labeled cell extract with a lectin immobilized on a slide glass, and sensitively detecting the weak interaction between the lectin and the reacted fluorescence-labeled sugar chain using a special detection scanner called evanescent wave excited fluorescence. Thus, the method has not been able to be used as a technique for detecting the location of undifferentiated stem cells in a state in which a three-dimensional structure such as a colony is maintained or a technique for separating undifferentiated stem cells and differentiated cells alive because the method can detect an undifferentiated stem cell marker but involves the grinding of cells themselves.

A lectin has been considered to be less easily applied to flow cytometry generally used for isolating cells because of having the general properties of low specificity and affinity for a ligand as described above; thus, the lectin has conventionally been not common as a tool for isolating cells and also as a probe for cell staining such as immunohistochemistry.

Against such a background, the present inventors happened to fluorescently label "rBC2LCN lectin," directly react the resultant with undifferentiated stem cells chemically fixed with 4% paraformaldehyde while adhering onto a plastic dish, and perform microscopic observation; as a result, it has been surprisingly found that whereas the fluorescence-labeled rBC2LCN lectin very strongly stained (fluorescently labeled) human ES cells and iPS cells maintaining an undifferentiated state, the lectin completely failed to react with feeder cells or differentiated cells.

Specifically, whereas the rBC2LCN lectin did not react with co-cultured feeder cells such as MEF and SNL cells, the lectin strongly reacted with ES cells and iPS cells maintaining an undifferentiated state. The rBC2LCN lectin also completely failed to react with ES cells and iPS cells differentiated by culture in the presence of retinoic acid, whereas the lectin specifically and strongly reacted with ES cells and iPS cells maintaining an undifferentiated state in the absence of retinoic acid.

rBC2LCN lectin combining such strong specificity and strong affinity for ligands goes beyond the common knowledge of conventional lectin and is a result unforeseen by the present inventors. The experimental results show that whereas the undifferentiation sugar chain marker "Fucα1-2Galβ1-3GlcNAc/GalNAc" is always present on the surface of undifferentiated stem cells, the undifferentiation sugar chain marker decreases as differentiation proceeds by the induction of differentiation, and disappears on complete differentiation. From this it can be expected that BC2LCN lectin functions as an excellent "undifferentiated stem cell-specific probe" for detecting the sugar chain "Fucα1-2Galβ1-3GlcNAc/GalNAc" specifically expressed on undifferentiated stem cells. For the purpose of the present invention, the probe "specifically" recognizing the sugar chain structure "Fucα1-2Galβ1-3GlcNAc/GalNAc" means that the probe has specificity to the extent of being capable of recognizing (or binding to) the sugar chain structure specifically expressed on undifferentiated cells.

A further experiment of the present inventors could confirm that when used as "undifferentiated stem cell-specific labeled probe," the rBC2LCN lectin by far surpassed an antibody to a conventionally used undifferentiation marker (SSEA4, Tra-1-60, Tra-1-81, Nanog, or Oct3/4) in all performances envisioned in practical use, such as a uniform, stable and highly reproducible ability to stain undifferentiated stem cells almost without observing background, and binding to the cell surface marker with high sensitivity and high specificity.

This shows that a simple technique conventionally used in an immunohistochemistry method using an antibody can be directly applied to the fluorescence-labeled BC2LCN lectin of the present invention. That is, cell/tissue staining using BC2LCN lectin of the present invention may be performed to confirm the presence/intensity of a label (for example, fluorescence) when the undifferentiated state of ES cells, iPS cells, or the like is evaluated or when the differentiated state is evaluated in inducing the differentiation of undifferentiated stem cells. At the time, not only a method using cultured cells by adhering onto a substrate such as a plastic dish can be applied but also a flow cytometry measurement method can be applied because it has been able to be confirmed that stem cells in an undifferentiated state can be suspended in a solution to enable labeling in suspension, enabling the provision of a system for more reliably evaluating the undifferentiated state. It has also been able to be confirmed that a cell sorter can be applied to the fluorescence-labeled cells in solution to efficiently separate labeled undifferentiated stem cells and unlabeled cells whose differentiation is advanced, with high speed.

The present invention has been accomplished by obtaining the above findings.

Thus, according to a first aspect, the present invention provides a method for determining differentiation of a cell comprising a step of contacting a test cell with a probe comprising a protein (A) or (B) below and a step of detecting the presence of binding of the probe to the test cells:
(A) a protein comprising the amino acid sequence shown in SEQ ID NO: 1 and recognizing a sugar chain structure of "Fucα1-2Galβ1-3GlcNAc" and/or "Fucα1-2Galβ1-3GalNAc;" and (B) a protein comprising an amino acid sequence showing 80% or more similarity to the amino acid sequence shown in SEQ ID NO: 1 and recognizing a sugar chain structure of "Fucα1-2Galβ1-3GlcNAc" and/or "Fucα1-2Galβ1-3GalNAc."

According to the method for determining differentiation of a cell, a presence or absence (or amount) of binding of the probe to the test cell is detected using a probe specifically reacting with undifferentiated stem cells, for example, based on a label labeled to the probe, as a result, the differentiation status of the test cells can be determined based on the presence or absence (or amount) of the binding, and then the presence or absence of undifferentiated stem cells can be detected.

Thus, for example, the use of stem cells treated for the maintenance of the undifferentiated state as test cells can confirm that the test cells maintain properties as stem cells, which can aid in the quality control of stem cells.

Alternatively, the use of a somatic cell subjected to a pluripotency induction treatment as a test cell can confirm that the test cell has been dedifferentiated to acquire properties as a stem cell, which can aid in the quality control of the resultant pluripotency-induced stem cells.

In addition, the use of stem cells subjected to a differentiation induction treatment as test cells can detect the contamination of the test cells with undifferentiated stem cells, which can aid in the quality control of the resultant differentiated cells.

The present invention also provides a cell separation method comprising a step of contacting a test cell with a probe comprising a protein (A) or (B) below and a step of separating a cell binding to the probe and a cell not binding thereto:
(A) a protein comprising the amino acid sequence shown in SEQ ID NO: 1 and recognizing a sugar chain structure of "Fucα1-2Galβ1-3GlcNAc" and/or "Fucα1-2Galβ1-3GalNAc;" and
(B) a protein comprising an amino acid sequence showing 80% or more similarity to the amino acid sequence shown in SEQ ID NO: 1 and recognizing a sugar chain structure of "Fucα1-2Galβ1-3GlcNAc" and/or "Fucα1-2Galβ1-3GalNAc."

This cell separation method can use a probe specifically reacting with undifferentiated stem cells to separate a cell having bound to the probe and a cell having not bound thereto to isolate undifferentiated stem cells in test cells or, conversely, to isolate differentiated cells.

According to the cell separation method, when the probe comprises an optically detectable label, the cell binding to the probe and the cell not binding thereto can be separated using a flow cytometer equipped with a cell sorter. When the probe comprises a magnetically detectable label, the cell binding to the probe and the cell not binding thereto can be separated using a magnetic cell separation apparatus.

In addition, the present invention provides a method for producing an induced pluripotent stem cell, comprising a step of subjecting a somatic cell to a pluripotency induction treatment, a step of contacting the pluripotency-induced cell with a probe comprising a protein (A) or (B) below, and a step of isolating a cell binding to the probe:
(A) a protein comprising the amino acid sequence shown in SEQ ID NO: 1 and recognizing a sugar chain structure of "Fucα1-2Galβ1-3GlcNAc" and/or "Fucα1-2Galβ1-3GalNAc;" and
(B) a protein comprising an amino acid sequence showing 80% or more similarity to the amino acid sequence shown in SEQ ID NO: 1 and recognizing a sugar chain structure of "Fucα1-2Galβ1-3GlcNAc" and/or "Fucα1-2Galβ1-3GalNAc."

This production method enables the confirmation of the acquisition of properties as stem cells by cells after dedifferentiation using a probe specifically reacting with undifferentiated stem cells and can produce pluripotency-induced stem cells not contaminated with a somatic cell.

The present invention also provides a method for producing differentiated cells, comprising a step of subjecting a stem cell to a differentiation induction treatment, a step of contacting the differentiation-induced cell with a probe comprising a protein (A) or (B) below, and a step of isolating cells not binding to the probe:
(A) a protein comprising the amino acid sequence shown in SEQ ID NO: 1 and recognizing a sugar chain structure of "Fucα1-2Galβ1-3GlcNAc" and/or "Fucα1-2Galβ1-3GalNAc;" and
(B) a protein comprising an amino acid sequence showing 80% or more similarity to the amino acid sequence shown in SEQ ID NO: 1 and recognizing a sugar chain structure of "Fucα1-2Galβ1-3GlcNAc" and/or "Fucα1-2Galβ1-3GalNAc."

This production method enables the detection of the contamination of cells with undifferentiated stem cells using a probe specifically reacting with undifferentiated stem cells and can produce differentiated cells not contaminated with undifferentiated stem cells.

According to a second aspect, the present invention encompasses the following inventions:

[1] a method for determining the differentiation status of stem cells using the intensity of a label as an indication, comprising a step of reacting a test stem cell with an undifferentiated stem cell-specific labeled probe comprising labeled BC2LCN lectin or a modified product thereof and then observing the intensity of the label;

[2] a method for detecting contamination with an undifferentiated cell, comprising a step of reacting stem cells subjected to a differentiation induction treatment with an undifferentiated stem cell-specific labeled probe comprising labeled BC2LCN lectin or a modified product thereof and then observing the intensity of the label;

[3] a method for the quality control of stem cells, comprising a step of reacting a stem cell subjected to a treatment for maintaining an undifferentiated state with an undifferentiated stem cell-specific labeled probe comprising labeled BC2LCN lectin or a modified product thereof and then observing the intensity of the label;

[4] a kit for determining the differentiation status of a test stem cell, comprising an undifferentiated stem cell-specific labeled probe comprising labeled BC2LCN lectin or a modified product thereof;

[5] an apparatus for determining the differentiation status of a test stem cell, comprising a means or an apparatus for supplying an undifferentiated stem cell-specific labeled probe comprising labeled BC2LCN or a modified product thereof to the test stem cell and a means or an apparatus for measuring the intensity of the label;

[6] a method for isolating only stem cells in an undifferentiated state, comprising a step of suspending stem cells in a solution, adding an undifferentiated stem cell-specific labeled probe comprising labeled BC2LCN lectin or a modified product thereof to the solution for reaction, and then separating a stem cell in an undifferentiated state using the intensity of the label as an indication;

[7] a method for isolating only differentiated cells, comprising a step of suspending differentiated cells partially contaminated with an undifferentiated stem cell in a solution, adding an undifferentiated stem cell-specific labeled probe comprising labeled BC2LCN lectin or a modified product thereof to the solution for reaction, and then removing a stem cell in an undifferentiated state using the intensity of the label as an indication;

[8] the method according to [6] above, wherein the stem cells in a solution are dedifferentiated iPS cells after dedifferentiation induction and wherein the method is used for obtaining iPS cells not contaminated with a somatic cell having failed to be dedifferentiated;

[9] the method according to [6], [7], or [8] above, wherein the label is a fluorescent dye label and wherein the method comprises a step of reacting with the undifferentiated stem cell-specific labeled probe, followed by supplying the resultant to a flow cytometer equipped with a cell sorter;

[10] the method according to [6], [7], or [8] above, wherein the label is a magnetic bead label and wherein the method comprises a step of reacting with the undifferentiated stem cell-specific labeled probe, followed by supplying the resultant to a magnetic cell separation apparatus;

[11] a kit for isolating or removing only stem cells in an undifferentiated state from stem cells suspended in a solution, comprising:
(1) an undifferentiated stem cell-specific labeled probe comprising fluorescence-labeled BC2LCN lectin or a modified product thereof; and
(2) a flow cytometer equipped with a cell sorter; and

[12] a kit for isolating or removing only stem cells in an undifferentiated state from stem cells suspended in a solution, comprising:
(1) an undifferentiated stem cell-specific labeled probe comprising magnetic bead-labeled BC2LCN lectin or a modified product thereof; and
(2) a means or an apparatus for separating magnetic cells.

According to the present invention, "protein comprising the amino acid sequence shown in SEQ ID NO: 1" encompasses "BC2LCN lectin" as a protein comprising the amino acid sequence shown in SEQ ID NO: 1 and "fusion protein of BC2LCN lectin" in which one or more other amino acid sequences are added to the amino acid sequence shown in SEQ ID NO: 1. In addition, the "protein comprising the amino acid sequence shown in SEQ ID NO: 1" can encompass a polymer of BC2LCN lectin and/or a fusion protein of BC2LCN lectin.

The term "similarity" is a concept encompassing both of the amino acid sequence identity between proteins and the amino acid sequence similarity between proteins in which consideration is given to properties of side chains of amino acids. Deletion, substitution, insertion, or addition in the amino acid sequence of a protein conserves the function of the protein provided that a certain identity is retained. Amino acids vary in properties such as molecular weight, acidity/alkalinity, and hydrophilicity/hydrophobicity depending on their side chains; however, a protein amino acid sequence substitution between amino acids, although they are different amino acids, closely analogous in the properties may conserve the function of the original protein.

Thus, "protein comprising an amino acid sequence showing similarity to the amino acid sequence shown in SEQ ID NO: 1" firstly means "modified BC2LCN lectin" comprising an amino acid sequence in which one or more amino acids in the amino acid sequence shown in SEQ ID NO: 1 are deleted, substituted, inserted, or added, "fusion protein of the modified BC2LCN lectin" in which one or more other amino acid sequences are added to the amino acid sequence of the lectin, and a polymer thereof.

The "protein comprising an amino acid sequence showing similarity to the amino acid sequence shown in SEQ ID NO: 1" secondly means "modified BC2LCN lectin" comprising an amino acid sequence in which one or more amino acids in the amino acid sequence shown in SEQ ID NO: 1 are substituted by amino acids closely analogous in the above-described properties, "fusion protein of the modified BC2LCN lectin" in which one or more other amino acid sequences are added to the amino acid sequence of the lectin, and a polymer thereof.

In addition, the "protein comprising an amino acid sequence showing similarity to the amino acid sequence shown in SEQ ID NO: 1" thirdly encompasses "modified BC2LCN lectin" comprising an amino acid sequence in which one or more amino acids are deleted, substituted, inserted, or added in the amino acid sequence shown in SEQ ID NO: 1 and one or more amino acids are substituted by amino acids closely analogous in properties in the amino acid sequence, "fusion protein of the modified BC2LCN lectin" in which one or more other amino acid sequences are added to the amino acid sequence of the lectin, and a polymer thereof.

The similarity of amino acid sequences can be calculated using a general-purpose analytical tool. For example, BLAST provided by the National Center for Biotechnology Information (NCBI) is available.

"Stem cells" means cells combining a capability capable of differentiating into specialized cells other than themselves (cell potency) and a capability of producing cells having the same properties as those of themselves even after cell division (self-renewal capability) ("undifferentiated stem cells" also has the same meaning).

"Undifferentiated state" means a state in which cells combine a capability capable of differentiating into specialized cells other than themselves and a self-renewal capability. "Treatment for maintaining an undifferentiated state" is treatment for maintaining the capability capable of differentiating into specialized cells other than themselves and the self-renewal capability so that stem cells do not lose these capabilities, and is not particularly limited; however, examples thereof include treatment such as the addition of bFGF or LIF to the cellular medium.

"Induced pluripotent stem cells" means cells which are originally somatic cells and have come to combine a capability capable of differentiating into cells having all properties composed of 3 germ layers (pluripotency) and a capability of producing cells having the same properties as those of themselves even after cellular division (self-renewal capability) by pluripotency induction treatment. The induced pluripotent stem cells encompass cells generally designated as iPS cells (induced pluripotent stem cells). The "pluripotency induction treatment" is treatment for imparting pluripotency and self-renewal capability and is not particularly limited; however, examples thereof include treatment such as introducing the 4 genes of Sox2, Oct3/4, Klf4, and Myc.

"Differentiated cells" means cells resulting from the change and specialization of relatively undifferentiated cells such as stem cells. A "differentiation induction treatment" is treatment for specializing relatively undifferentiated cells such as stem cells and is not particularly limited; however, examples thereof include treatment such as the addition of a growth factor such as BMP or Wnt or a differentiation-inducing factor such as retinoic acid to cellular medium and the introduction of a gene such as MyoD.

Advantageous Effect of Invention

BC2LCN lectin according to the present invention can be used as an excellent "undifferentiated stem cell-specific probe" capable of detecting "Fucα1-2Galβ1-3GlcNAc/GalNAc" sugar chain specifically expressed on undifferentiated stem cells. Only stem cells in an undifferentiated state can be specifically and sensitively labeled by labeling the "undifferentiated stem cell-specific probe" of the present invention with a labeling substance and directly reacting the resultant with test cells. This enables the differentiation status of the test cells to be simply and effectively evaluated. The undifferentiated stem cell-specific probe of the present invention can be used to separate cells in an undifferentiated state and cells whose differentiation is advanced; thus, the probe can be expected to be applied to regeneration medicine, biologics, and the like.

DESCRIPTION OF EMBODIMENTS

Figure 1:
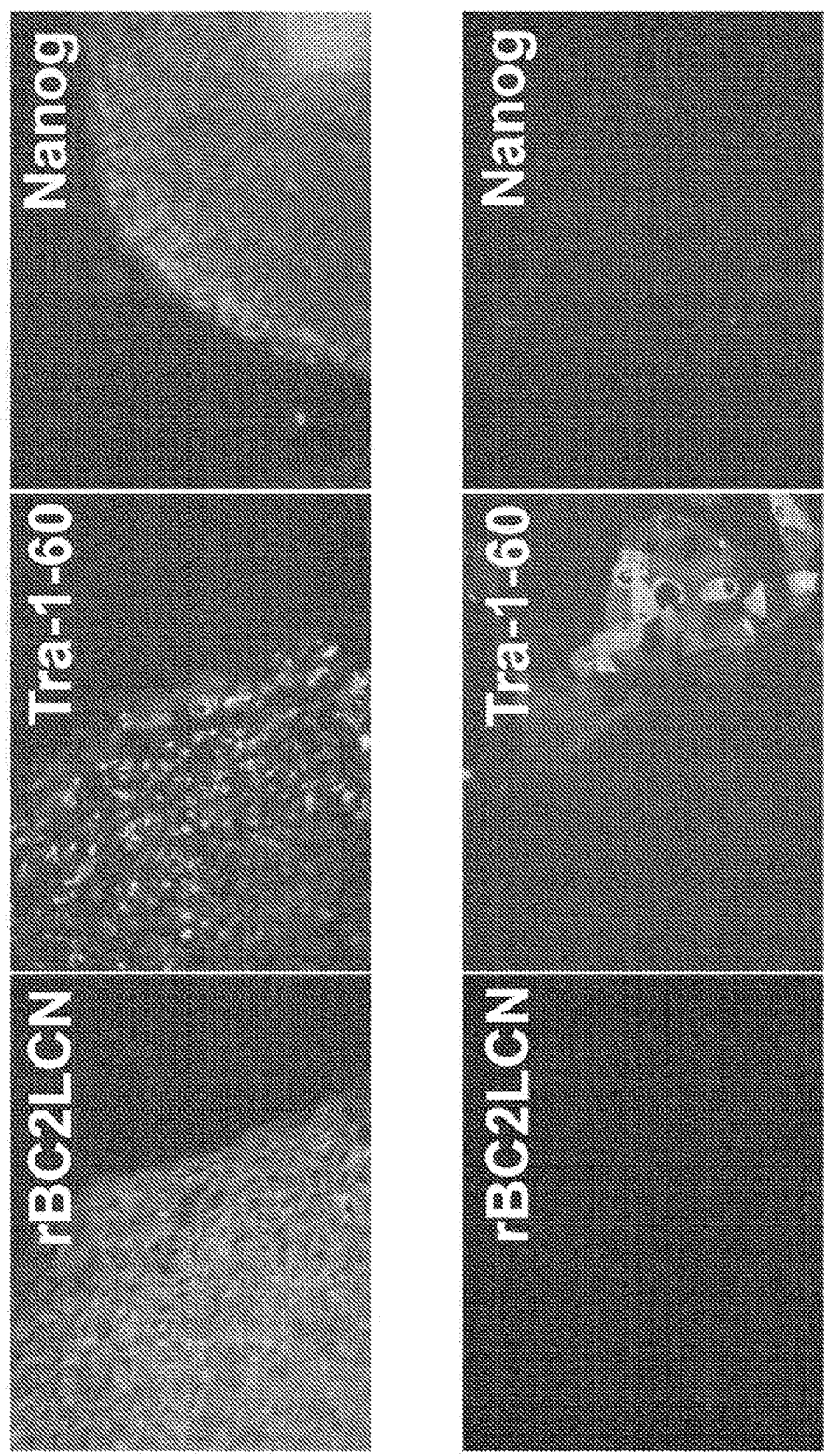
FIG. 1 is a series of photographs showing the results of staining undifferentiated ES cells (KhES-1 strain) and ES cells subjected to a differentiation induction treatment (retinoic acid treatment) with Cy3-labeled rBC2LCN lectin and known undifferentiation markers.

1. Undifferentiation Sugar Chain Marker Specifically Expressed on Undifferentiated Cell Surface Recognized by "Undifferentiated Stem Cell-Specific Probe" of Present Invention The "undifferentiated stem cell-specific probe" of the present invention simultaneously recognizes "Fucα1-2Galβ1-3GlcNAc (H type 1 sugar chain)" and "Fucα1-2Galβ1-3GalNAc (H type 3 sugar chain)" (hereinafter also together referred to as "Fucα1-2Galβ1-3GlcNAc/GalNAc"). "Fucα1-2Galβ1-3GlcNAc/GalNAc" has the following structures, which are each a sugar chain structure of a glycoprotein or a glycolipid prominently expressed on the cell surface of human ES/iPS cells.

Only after observation using the "undifferentiated stem cell-specific probe" of the present invention has it been able to be confirmed that these 2 types of sugar chains are always presented on the surface of cells in an undifferentiated state such as ES cells and iPS cells, while being always not presented on the surface of differentiated somatic cells, namely that these sugar chain ligands are always presented on the surface of cells only when the cells are in an undifferentiated state.

For the sugar chain structure of "Fucα1-2Galβ1-3GlcNAc", the hydroxyl group of position 4 of GlcNAc may be substituted by a monosaccharide (preferably fucose) or a branched or non-branched oligosaccharide chain (preferably a sugar chain consisting of 2 to 5 saccharides). The sugar chain structure is a sugar chain binding to the nonreducing terminus of a glycoprotein, a glycolipid, a saccharide, or the like at position 1 of GlcNAc as a membrane constituent on the surface of undifferentiated stem cells. Thus, the sugar chain structure can be represented as formula 1:

[Formula 1]

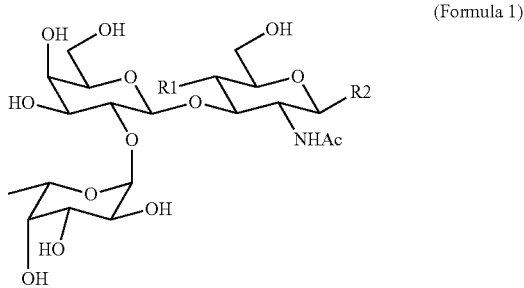

(Formula 1)

wherein R1 represents an OH group or any sugar chain, such as a 4αFuc group and R2 represents an OH group or any sugar chain, protein, lipid, or another molecule.

Similarly, for the sugar chain structure of "Fucα1-2Galβ1-3GalNAc", the hydroxyl group of position 1 of GalNAc may be substituted by a branched or non-branched oligosaccharide chain (preferably a sugar chain consisting of 2 to 5 saccharides). The sugar chain structure is a sugar chain binding to the nonreducing terminus of a glycoprotein, a glycolipid, a saccharide, or the like at position 1 of GalNAc as a membrane constituent on the surface of undifferentiated stem cells; thus, it also binds to the nonreducing terminus of an OH group or another saccharide, protein or lipid, or a different molecule at position 1 of GalNAc. Thus, the sugar chain structure can be represented as formula 2:

[Formula 2]

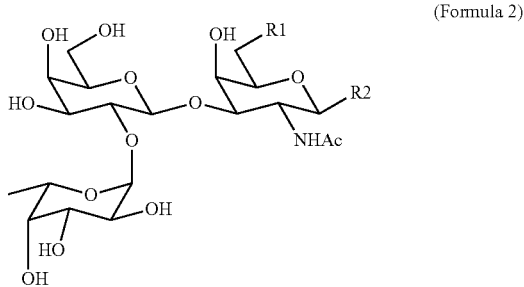

(Formula 2)

wherein R1 represents an OH group or any sugar chain such as a Galβ1-4Glc group and R2 represents an OH group or any sugar chain, protein, lipid, or another molecule.

2. "Undifferentiated Stem Cell-Specific Probe" of Present Invention

The "undifferentiated stem cell-specific probe" of the present invention consists of the following protein (A) or (B). The probe preferably contains a detectable label.

(A) A protein comprising the amino acid sequence shown in SEQ ID NO: 1 and recognizing a sugar chain structure of "Fucα1-2Galβ1-3GlcNAc" (Formula 1) and/or "Fucα1-2Galβ1-3GalNAc" (Formula 2).

(B) A protein comprising an amino acid sequence showing 80% or more similarity to the amino acid sequence shown in SEQ ID NO: 1 and recognizing a sugar chain structure of "Fucα1-2Galβ1-3GlcNAc" (Formula 1) and/or "Fucα1-2Galβ1-3GalNAc" (Formula 2).

"BC2LCN lectin" is a lectin found in a gram-negative bacterium (*Burkholderia cenocepacia*) and corresponds to the N-terminal domain of a protein called BC2L-C (GenBank/NCBI-GI Accession No. YP_002232818) (Non Patent Literature 3). BC2LCN is known to show structural similarity to TNF-like protein and form a trimer. Analysis using a sugar chain array has demonstrated that the lectin exhibits binding specificity to "Fucα1-2Galβ1-3GlcNAc (H type 1 sugar chain)" and "Fucα1-2Galβ1-3GalNAc (H type 3 sugar chain)". Analysis using a sugar chain array has also demonstrated that the lectin exhibits binding property to "Lewis b sugar chain (Fucα1-2Galβ1-3(Fucα1-4)GlcNAc)" or "Globo H sugar chain (Fucα1-2Galβ1-3GalNAcβ1-3Galα1-4Galβ1-4Glc)" including these sugar chain structures as a sugar chain structure containing H type 1 and H type 3 sugar chains.

"BC2LCN lectin" can be bulk-produced even by transformed bacteria. Specifically, BC2LCN gene encoding the amino acid sequence of GenBank/NCBI-GI Accession No. YP_002232818 (Genome ID: 206562055) (SEQ ID NO: 1) can be used, expressed in transformed *Escherichia coli* after properly optimizing it for the host, and purified by a conventional protein purification means. The recombinant BC2LCN obtained by this method contains no sugar chain. BC2LCN according to the present invention may be recombinant BC2LCN having a sugar chain obtained by a gene recombination technique using, for example, a eukaryote (eukaryotic cells), such as yeast, as a host. However, preferred is BC2LCN lectin having no sugar chain in view of ease of condition setting and the like in performing the method of the present invention. The cells used as a host in obtaining recombinant BC2LCN lectin are preferably bacteria (prokaryote, prokaryotic cells) such as *Escherichia coli* in view of ease of handling and the like. Hereinafter, mere "BC2LCN" sometimes includes both meanings: BC2LCN having a sugar chain and BC2LCN having no sugar chain. In addition, "rBC2LCN" means recombinant BC2LCN.

For (A) above, the "protein comprising the amino acid sequence shown in SEQ ID NO: 1" may be "BC2LCN lectin" as a protein consisting of the amino acid sequence shown in SEQ ID NO: 1 or "fusion protein of BC2LCN lectin" in which one or more other amino acid sequences are added to the amino acid sequence shown in SEQ ID NO: 1.

The fusion protein is not particularly limited; however, examples thereof include a fusion protein with a protein bound to an additional sequence for protein purification, such as a histidine tag, or a fluorescent protein, such as GFP, and a fusion protein with an enzyme, such as HRP or LacZ. In addition, the "protein comprising the amino acid sequence shown in SEQ ID NO: 1" may also be a polymer of BC2LCN lectin and/or a fusion protein of BC2LCN lectin.

For (B) above, the "protein comprising an amino acid sequence showing similarity to the amino acid sequence shown in SEQ ID NO: 1" may be firstly "modified BC2LCN lectin" consisting of an amino acid sequence in which one or more amino acids in the amino acid sequence shown in SEQ ID NO: 1 are deleted, substituted, inserted, or added, "fusion protein of the modified BC2LCN lectin" in which one or more other amino acid sequences are added to the amino acid sequence of the lectin, or a polymer thereof.

Examples of the modified BC2LCN lectin include a protein in which the amino acid deletion, substitution, insertion, or addition increases a binding property to the sugar chain structure of "Fucα1-2Galβ1-3GlcNAc" (Formula 1) and/or "Fucα1-2Galβ1-3GalNAc" (Formula 2). The modified BC2LCN lectin does not require the whole length corresponding to SEQ ID NO: 1 and may be, for example, a protein consisting of only an amino acid sequence as a recognition site for the sugar chain structure of "Fucα1-2Galβ1-3GlcNAc" (Formula 1) and/or "Fucα1-2Galβ1-3GalNAc" (Formula 2) in the amino acid sequence of BC2LCN lectin. In addition, the modified BC2LCN lectin may be a protein in which the amino acid deletion, substitution, insertion, or addition increases thermal stability, stability to acid and alkali, resistance to protease, and the like while allowing the maintenance of a binding property to the sugar chain structure of "Fucα1-2Galβ1-3GlcNAc" (Formula 1) and/or "Fucα1-2Galβ1-3GalNAc" (Formula 2).

The "protein comprising an amino acid sequence showing similarity to the amino acid sequence shown in SEQ ID NO: 1" may be secondly "modified BC2LCN lectin" consisting of an amino acid sequence in which one or more amino acids in the amino acid sequence shown in SEQ ID NO: 1 are substituted by amino acids closely analogous in properties, "fusion protein of the modified BC2LCN lectin" in which one or more other amino acid sequences are added to the amino acid sequence of the lectin, or a polymer thereof.

Examples of the modified BC2LCN lectin include a protein in which conservative substitution is performed between amino acids having uncharged polar side chains (for example, asparagine, glutamine, serine, threonine, and tyrosine). In addition, examples of the conservative substitution include substitution between amino acids having basic side chains (for example, lysine, arginine, and histidine), between amino acids having acidic side chains (for example, aspartic acid and glutamic acid), and between amino acids having non-polar side chains (for example, glycine, alanine, valine, leucine, isoleucine, proline, phenylalanine, methionine, tryptophan, and cysteine).

The "protein comprising an amino acid sequence showing similarity to the amino acid sequence shown in SEQ ID NO: 1" may be thirdly "modified BC2LCN lectin" consisting of an amino acid sequence in which one or more amino acids are deleted, substituted, inserted, or added in the amino acid sequence shown in SEQ ID NO: 1 and one or more amino acids are substituted by amino acids closely analogous in properties in the amino acid sequence, "fusion protein of the modified BC2LCN lectin" in which one or more other amino acid sequences are added to the amino acid sequence of the lectin, or a polymer thereof.

For these modified BC2LCN lectins, the similarity to the amino acid sequence shown in SEQ ID NO: 1 is not particularly limited provided that a function is maintained which specifically recognizes the sugar chain structure of "Fucα1-2Galβ1-3GlcNAc" (Formula 1) and/or "Fucα1-2Galβ1-3GalNAc" (Formula 2); however, the similarity is, for example, considered to be 80% or more, preferably 90% or more, more preferably 95% or more. In the amino acid sequence shown in SEQ ID NO: 1, the number of deleted, substituted, inserted, or added amino acids is not particularly limited provided that the above-described function is maintained; however, the number is, for example, considered to be 20 or less, preferably 10 or less, more preferably 5 or less.

Hereinafter, mere "BC2LCN" or "rBC2LCN" sometimes refers to both BC2LCN lectin and modified BC2LCN lectin (a modified product).

3. Analysis Method and Isolation Method for Undifferentiated Stem Cell Using "Undifferentiated Stem Cell-Specific Probe" of Present Invention (1) Method for Labeling BC2LCN Lectin or Modified Product Thereof BC2LCN or a modified product thereof of the present invention may be labeled with a detectable labeling substance. To label BC2LCN or a modified product thereof of the present invention, fluorescence, enzyme, biotin, magnetic bead, or the like is used by an ordinary method. A preferable labeling substance species varies depending on use of BC2LCN or a modified product thereof. For example, fluorescent labeling is preferable for cell staining and flow cytometry analysis and preferable examples of a fluorescent dye used at that time can include "Cy3," "Cy5," "FITC," "Hilyte Fluor™ 647," "phycoerythrin," and "allophycocyanin" In labeling BC2LCN or a modified product thereof, the known method of Hohsaka et al. (see Non Patent Literature 5) can be used for introducing a fluorescence-labeled amino acid into any site in an amino acid sequence to prepare a variant in which the fluorescence-labeled amino acid is introduced into a particular site in BC2LCN lectin. In use for cell separation, labeling with magnetic beads besides the fluorescent dye is also useful. The use of the technique of Veritas Corporation (http://www.veritastk.co.jp/news.php?id=51) or the like can prepare magnetic bead-labeled BC2LCN lectin using magnetic beads having a chemical functional group binding to a primary amino group, an aldehyde group, or a ketone group on a ligand. In verifying distribution in a large tissue not to transmit light, enzymes such as "horseradish peroxidase" and "alkaline phosphatase" or "detection system utilizing biotin avidin reaction" can be used. At that time, the use of the technique of Dojindo Laboratories (http://www.cosmobio-.co.jp/product/koutai_assei/cat436/01440001__2.asp?entry id=3109) or the like can label an enzyme or biotin activated with an NHS group or a maleimide group on a primary amino group ($NH_2$) or a thiol group (SH group, sulfhydryl group) of BC2LCN lectin.

(2) Test Stem Cell of Interest

The test cells of interest herein are "stem cells" in an undifferentiated state, or cells specifically differentiated into various tissues by the induction of differentiation of the cells (hereinafter sometimes described as "differentiated cells"). "Stem cells" here means pluripotent stem cells in an undifferentiated state and encompass stem cells dedifferentiated by introducing a stem cell-specific expression gene and the like into somatic cells (iPS cells and the like) in addition to various somatic stem cells such as embryonic stem cells (ES cells), hematopoietic stem cells, neural stem cells, and skin tissue stem cells.

An adherent cell culture method in a culture vessel is typically used as a method for culturing stem cells. In adherent culture, there are a case where stem cells are caused to adhere to a plastic dish uncoated or coated with feeder cells or a coating material such as an extracellular matrix extract, and a case where stem cells are floated in a culture vessel by causing to adhere to the bead surface or the like. There may also be a suspension cell culture method which involves suspending and directly floating stem cells in a culture medium.

Stem cells including ES cells are considered to be controlled by a common mechanism in a substantial proportion of mammals as well as humans; thus, the stem cells of the present invention can be applied also for the case of using stem cells derived from mammals other than humans, such as monkey, pig, cow, goat, sheep, mouse, and rat.

Here, practicing the present invention by selecting iPS cells as test stem cells also enables determination in inducing the differentiation of iPS cells, the determination of a dedifferentiated state in inducing dedifferentiation into iPS cells from differentiated somatic cells such as fibroblasts, and the isolation of only cells having become iPS cells by dedifferentiation.

The undifferentiated stem cell-specific probe of the present invention binds to live stem cells as well as stem cells killed by chemical fixation. The probe also binds to adhering stem cells and floating stem cells. Thus, these cells can be labeled using an undifferentiated stem cell-specific labeled probe labeled with a detectable labeling substance. Here, the term "floating stem cells" encompasses "floating-cultured stem cells" as well as "stem cells floated by protease treatment after adherent culture," and there are both cases of cells in a culture medium and cells in a solution from which medium components are removed, such as buffer or saline. The term "adhering stem cells" encompasses stem cells in a state subjected to adherent culture on a substrate such as a dish as well as stem cells caused to adhere to a substrate such as beads and floating-cultured.

(3) Method for Analyzing Stem Cell Sample (Method for Determining Differentiation of Cell According to Present Invention)

The method for determining differentiation of a cell according to the present invention comprises a step of contacting the undifferentiated stem cell-specific probe with test cells (contact procedure) and a step of detecting the presence (or amount) of the binding of the test cells to the probe (detection procedure). The undifferentiated stem cell-specific probe used for the method for determining differentiation of a cell is preferably labeled with a detectable labeling substance. Then, the presence (or amount) of the binding of the probe to the test cells can be detected, for example, based on the label bound to the probe to determine the differentiation status of the test cells based on the presence (or amount) of the binding to detect the presence or absence of undifferentiated stem cells in the test cells (determination procedure). Specifically, when the probe binds to the test cells (or the amount of binding is large), the test cells can be determined to be undifferentiated cells. When the probe does not bind to the test cells (or the amount of binding is small), the test cells can be determined to be differentiated cells. In the method for determining differentiation of a cell according to the present invention, persons performing the contact procedure, the detection procedure, and the determination procedure may be identical or different. The procedures may be continuously or discontinuously performed.

(3-1) Contact Procedure

For the contact procedure, when stem cells are cultured in a state adhering to a substrate in a culture vessel, a method for supplying the undifferentiated stem cell-specific labeled probe to stem cells in a solution involves supplying a labeled probe solution to the solution covering the surface thereof, enabling the labeling of only stem cells in an undifferentiated state without being affected by the presence or absence of feeder cells or the like. Even when stem cells are cultured in a suspended state, the supply of a labeled probe solution to the solution can label only stem cells in an undifferentiated state.

Particularly when only stem cells in an undifferentiated state are isolated, the high specificity and affinity of the undifferentiated stem cell-specific labeled probe of the present invention, enabling the labeling of even cells in a suspension can be said to be particularly advantageous characteristics to reduce burden on stem cells and simply perform the isolation. Specifically, when stem cells is subjected to adherent culture or floating culture, a solution of the undifferentiated stem cell-specific labeled probe of the present invention can be added to a culture medium of stem cells, followed by measuring the amount of the label on the stem cell surface to accurately evaluate the degree of differentiation of the stem cells. Cells in a suspension can also be directly applied to the isolation of undifferentiated stem cells using a cell sorter or a magnetic cell separation apparatus. If necessary, the solution can be replaced with buffer, saline, or the like to easily remove the influence of medium components. The amount of the label on the stem cells can be measured even in the case of dead cells as in the case of live cells; thus, the cells are chemically fixed with formalin or the like in advance to simplify the handling thereof. Particularly, depending on the type of a labeling substance species (for example, when alkaline phosphatase is selected), the chemical fixation of cells with formalin is essential to eliminate alkaline phosphatase activity in the cells.

(3-2) Detection/Determination Procedure (When Applied to Stem Cell Caused to Adhere to Substrate)

The "undifferentiated stem cell-specific probe" of the present invention can be applied to the case of distinguishing between stem cells in an undifferentiated state and differentiation-induced cells when cultured on a beads-shaped, hollow fiber shaped, or plate-shaped substrate. Here, it is preferable to add an undifferentiated stem cell-specific labeled probe in which the undifferentiated stem cell-specific probe is labeled with a labeling substance to a solution in which the substrate is present, because the addition facilitates detection. Here, the term "solution" may be a culture medium, or buffer, saline, or the like after removing medium components.

To perform the method for determining differentiation of a cell according to the present invention, by way of example, reactivity with the sugar chains represented by the above (Formula 1) and (Formula 2) specifically expressed on the undifferentiated cell surface may be detected through the label derived from the undifferentiated stem cell-specific labeled probe using, for example, a fluorescence microscope or ELISA to detect undifferentiated cells. According to the analysis method, for example, stem cells in an undifferentiated state are subjected to a differentiation induction treatment, followed by sampling cells to perform the above detection. The cell group subjected to a differentiation induction treatment can be evaluated as that consists of only differentiated cells not any longer contaminated with undifferentiated cells if the label derived from the undifferentiated stem cell-specific labeled probe is no longer detected (have decreased to the same level as the background value). The same differentiation induction treatment can also be performed to rapidly obtain differentiated cells having no risk of contamination with undifferentiated cells in large quantity. The chemical fixation treatment of cells may be required, for example, in using the undifferentiated stem cell-specific labeled probe of the present invention as a labeled probe labeled with alkaline phosphatase.

Here, the method for "differentiation induction" of stem cells into neuronal cells, digestive system cells, or the like may be any method; for example, various well-known methods can be applied, including a method for culturing stem cells in the presence of retinoic acid to differentiate them into nervous system cells and a method for forming heart muscle cells from stem cells using a humoral factor such as noggin. Because the expression level of the cell surface undifferentiation sugar chain marker of the present invention on the surface of differentiated cells is of a negligible extent, noise is expected to be extremely reduced under any differentiation induction conditions.

For the quality control of stem cells whose undifferentiated state is desired to be maintained, the method for determining differentiation of a cell of the present invention is performed by collecting a cell sample periodically or as needed to enable it to be confirmed whether cells are maintained in the undifferentiated state.

When differentiated somatic cells such as fibroblasts are subjected to dedifferentiation induction into iPS cells, the method for determining differentiation of a cell according to the present invention can be used to determine whether or not the dedifferentiation of the somatic cells has occurred for the establishment of iPS cells.

(3-3) Detection/Determination Procedure (when Applied to Stem Cells Suspended in Solution)

The "undifferentiated stem cell-specific probe" of the present invention can also be applied to the case of distinguishing between stem cells and cells differentiated therefrom in a solution. In this case, the undifferentiated stem cell-specific probe is added to the solution. Here, the term "solution" may be a culture medium, or buffer, saline, or the like after removing medium components.

Methods for distinguishing between undifferentiated stem cells and differentiated cells in a solution by the method for determining differentiation of a cell according to the present invention include a method which involves using the "undifferentiated stem cell-specific probe" of the present invention to perform, for example, a well-known flow cytometry measurement method. For example, when flow cytometry is performed using "undifferentiated stem cell-specific labeled probe" in which the "undifferentiated stem cell-specific probe" of the present invention is labeled with a labeling substance, a reliable system for evaluating an undifferentiated state can be provided by dissociating a stem cell colony by enzyme treatment, reacting the resultant with the undifferentiated stem cell-specific labeled probe, and performing flow cytometry analysis using a FACS apparatus.

(4) Method for Isolating Undifferentiated Stem Cell or Differentiated Cell

BC2LCN lectin combines strong specificity and strong affinity for the undifferentiation sugar chain markers as described above and shows extremely high binding strength to stem cells as will be described later; thus, these properties can be utilized to separate differentiated cells and undifferentiated stem cells. The method for separating cells according to the present invention comprises a step of contacting a test cell with an undifferentiated stem cell-specific probe and a step of separating a cell binding to the probe and a cell not binding thereto. According to this cell separation method, undifferentiated stem cells in test cells can be isolated, or, conversely, differentiated cells can be isolated, by using a probe specifically reacting with the undifferentiated stem cells to separate cells having bound to the probe and cells having not bound thereto.

A conventionally used cell separation method can be used as a specific method for separating cells without any particular limitation provided that it is a method capable of separating cells having bound to the undifferentiated stem cell-specific probe of the present invention (undifferentiated stem cells) and cells having not bound to the probe. Specific conditions therefor may be set so that the cells having bound to the undifferentiated stem cell-specific probe of the present invention are separated from the cells having not bound to the probe, and other conditions may be according to methods known per se.

For example, the case of using B/F separation may be performed as follows. That is, test cells can be contacted with the undifferentiated stem cell-specific probe of the present invention immobilized to a solid phase, followed by separating the solid phase and the liquid phase to separate cells having bound to the probe and cells having not bound to the probe.

Well-known flow cytometry techniques can also be applied to the cell separation method of the present invention. For example, when test cells are contacted with "undifferentiated stem cell-specific labeled probe" in which the "undifferentiated stem cell-specific probe" of the present invention is labeled with a detectable labeling substance, the probe binds only to stem cells in an undifferentiated state; thus, the undifferentiated stem cells are directly labeled with a fluorescent label or the like. Specifically, a reliable system for evaluating an undifferentiated state can be provided by dissociating a stem cell colony by enzyme treatment, reacting the resultant with the undifferentiated stem cell-specific labeled probe, and performing a flow cytometry analysis using a FACS apparatus.

Among flow cytometry techniques, a method for measuring scattered light, for example, a well-known method for measuring forward-scattered light and side-scattered light can be performed to separate cells having bound to the undifferentiated stem cell-specific probe of the present invention and cells having not bound to the probe using the probe without labeling with a labeling substance.

In addition, for example, using a substance having affinity for a substance to be analyzed (a so-called affinity ligand), various methods have been developed which utilize a change in the electrophoretic mobility of the object substance resulting from the interaction between the object substance and the affinity ligand for separation and analysis. Accordingly, this method can be used to separate cells having bound to an undifferentiated stem cell-specific probe and cells having not bound to the probe.

Cells having bound to the probe (cells binding to the probe) can be separated from cells having not bound to the probe (cells not binding to the probe) by applying, for example, an affinity electrophoresis method using an insoluble support, such as agarose gel or polyacrylamide gel, having an affinity ligand coupled thereto, a lectin affinity electrophoresis method involving performing electrophoresis using a focusing gel or the like containing lectin, affinophoresis using an affinity ligand bound to an ionic polymer, or a gel shift assay.

When the separation method of the present invention is performed using lectin affinity electrophoresis, a method is available which involves using the undifferentiated stem cell-specific probe of the present invention in place of lectin to perform electrophoresis using a focusing gel or the like containing the probe. In capillary electrophoresis to be described later, when the undifferentiated stem cell-specific probe of the present invention is present in a liquid (buffer) in the capillary to perform electrophoresis, undifferentiated stem cells bind to the undifferentiated stem cell-specific probe in the capillary without the binding of the other cells to the probe on the way for test cells to migrate through the capillary by electrophoresis. Thus, cells having bound to the probe and cells having not bound to the probe can be separated by utilizing the difference in mobility between both cells.

Cells can also be separated using a separation method utilizing a phenomenon in which the placement of a substance in a non-uniform alternate current electric field causes positive and negative polarization in the substance and produces a force by which the substance migrates, the so-called dielectrophoretic force (H. A. Pohl: "Dielectrophoresis," Cambridge Univ. Press (1978), T. B. Jones: "Electromechanics of Particles," Cambridge Univ. Press (1995), and the like). For this separation method, the amount of the dielectrophoretic force depends on the size/dielectric property of the substance (particle); thus, the dielectrophoresis method can be used to separate cells having bound to the undifferentiated stem cell-specific probe of the present invention and cells having not bound to the probe (for example, Japanese Patent No. 4671084).

In addition, cells having bound to the undifferentiated stem cell-specific probe of the present invention and cells having not bound to the probe can be separated by performing a capillary electrophoresis method involving using a capillary (narrow tube) 1 mm or less in inside diameter produced using Teflon (registered trademark), silica, or the like as a material as a separation column to utilize the difference in electric charge between substances in a high electric field for separation, a capillary column chromatography method involving using the same capillary to utilize the difference in the interaction between a column support and a substance for separation, or the like.

Further, cells having bound to the undifferentiated stem cell-specific probe of the present invention and cells having not bound to the probe can be separated by a method involving using a permeable filter for separation, a method involving separation by difference in sedimentation rate, a method involving separation by density-gradient centrifugation, or a method involving separation using ferrofluid.

The above separation methods include a method which involves performing the operation of separating a bound product (complex) of undifferentiated cells and an undifferentiated cell-specific probe and cells having not bound to the probe by using a so-called separation improver. This method enables the free adjustment of the elution position of the complex of undifferentiated cells and an undifferentiated cell-specific probe by properly selecting and using a separation improver, in other words, can clearly separate the complex and the cells having not bound to the probe by binding a suitable separation improver to the complex (Japanese Patent Laid-Open Nos. 06-066800, 07-191027, 2001-165905, and the like). When the separation improver is used, the separation improver bound to the undifferentiated stem cell-specific probe of the present invention may be used.

It suffices to properly select and use such a separation improver with the separation principle (size, hydrophobicity, isoelectric point, electric charge, and the like) of the performed separation method in mind. A specific example of the separation improver used, a method for binding the separation improver to the undifferentiated stem cell-specific probe of the present invention, an actual operation of separation of the complex, and the like may be properly selected based on well-known methods.

Only undifferentiated stem cells or only differentiated cells can be isolated by using a cell sorter in combination with the above cell separation method, for example, by using a flow cytometer equipped with a cell sorter. Specifically, only undifferentiated stem cells (or only differentiated cells) can be isolated since a stem cell colony can be dissociated by enzyme treatment, followed by reacting the resultant with the undifferentiated stem cell-specific probe and separating and collecting cells alive by a flow cytometry method.

When the undifferentiated stem cell-specific probe of the present invention labeled with magnetic beads is used, a stem cell colony is dissociated by enzyme treatment and reacted with the undifferentiated stem cell-specific magnetic bead-labeled probe, and supplied to a magnetic cell separation apparatus, as a result, only stem cells in an undifferentiated state (or only differentiated cells) can be separated and collected.

After separating cells by the separation method of the present invention, it may be confirmed by performing the method for determining differentiation of a cell of the present invention that desired undifferentiated stem cells or differentiated cells have been able to be recovered.

The differentiated cells isolated by the present invention can subsequently be used for the intended use. The undifferentiated stem cells isolated by the present invention have bound to the undifferentiated stem cell-specific probe of the present invention. The present inventors have confirmed that several days of culture results in little detection of fluorescence in the undifferentiated stem cells having bound to the undifferentiated stem cell-specific fluorescence-labeled probe. The probe disappeared from the undifferentiated stem cells during cell culture although the details are uncertain. As seen from this, the undifferentiated stem cells isolated by the present invention can be cultured under conditions of containing no undifferentiated stem cell-specific probe for several days (3 to 5 days) to obtain cells having not bound to the probe, which can subsequently be used for the intended use. Cells having not bound to the probe can be obtained by separating the probe from the undifferentiated stem cells isolated by the present invention by a well-known method for separating sugar chain from lectin.

(5) Binding Strength of "Undifferentiated Stem Cell-Specific Labeled Probe" of Present Invention to Sugar Chain (5-1) Measurement Method The binding strength between a substance having an activity of binding to a sugar chain such as lectin and a sugar chain is generally expressed as "dissociation constant." According to the present invention, the "sugar chain binding strength" of the undifferentiated stem cell-specific labeled probe of the present invention is measured by utilizing a flow cytometry method. Specifically, 0.01, 0.005, 0.002, 0.001, 0.0005, 0.0002, and 0.0001 mg/ml of undifferentiated stem cell-specific fluorescence-labeled probe solutions are prepared, and stem cell colonies are dissociated by enzyme treatment and reacted therewith to measure signal values. The results obtained are reciprocally plotted to calculate the Michaelis constant, which is considered to be an approximate value for the dissociation constant.

(5-2) Measurement Result

When the binding strength between rBC2LCN lectin and "Fucα1-2Galβ1-3GlcNAc/GalNAc" as its target sugar chain was measured by frontal affinity chromatography before studying the present invention, the dissociation constant was Kd=4.0.E−0.5 (described in PCT/JP2012/006983 as an prior application of the present inventors), which was comparable to the typical dissociation constant between lectin and sugar chain, not showing particularly high binding strength.

However, according to the present invention, when labeled BC2LCN lectin has been applied to undifferentiated stem cells as an undifferentiated stem cell-specific labeled probe, it has been expected from the results of observation by staining that the binding strength therebetween is as extremely high as not expected from the common binding between lectin and sugar chain.

Accordingly, when the dissociation constant between labeled rBC2LCN lectin and undifferentiated stem cells has been measured by a measurement method using the above-described flow cytometry method, the constant has been found to be as low (Kd=2.0.E−07) as not predicted from the actual dissociation constant between "rBC2LCN lectin" and "Fucα1-2Galβ1-3GlcNAc/GalNAc" sugar chain. The value of dissociation constant has also showed that BC2LCN lectin has extremely high binding strength to undifferentiated stem cells.

(6) Lack of Cytotoxicity in "Undifferentiated Stem Cell-Specific Labeled Probe" of Present Invention (6-1) Maintenance of Proliferative Activity of Stem Cell Even Under Long-Term Culture in Presence of "Undifferentiated Stem Cell-Specific Labeled Probe"

(a) Measurement Method

Because the cytotoxic potential in cells is best reflected in the proliferative capacity of the cells, the proliferative activity of stem cells in a medium containing "undifferentiated stem cell-specific labeled probe" has been measured by the morphological observation of colonies also in the present invention. Specifically, rBC2LCN lectin used in "undifferentiated stem cell-specific labeled probe" of the present invention has been added in a concentration of 1, 10, or 100 µg/ml to a medium of undifferentiated stem cells during culture and the cells have been cultured for 3 days. Then, the morphological observation of colonies has been performed to verify whether or not the proliferative activity of the stem cells is maintained. Simultaneously, fluorescence-labeled rBC2LCN lectin has been added to a medium of undifferentiated stem cells during culture to perform the same observation. Here, the amount of addition of 1 µg/ml is the maximum concentration used in actual vital staining; if even addition in a concentration of 10 to 100 times the amount of addition is not observed to decrease the proliferative activity, the lack of cytotoxicity can be verified.

(b) Measurement Result

As will be described later in Examples, even the colonies cultured in the presence of a highest concentration (100 µg/ml) of rBC2LCN or fluorescence-labeled rBC2LCN have been able to be confirmed to have the same morphology and size as those of untreated colonies. This has shown that even long-term culture in the presence of "undifferentiated stem cell-specific labeled probe" results in the maintenance of the proliferative activity of stem cells, confirming the lack of cytotoxicity of the probe.

(6-2) No Change in Undifferentiation Capability of Stem Cell Even Under Long-Term Culture in Presence of "Undifferentiated Stem Cell-Specific Labeled Probe"

(a) Measurement Method

The gene expression analysis of undifferentiated stem cells cultured in the same way as in (6-1) above has been exhaustively performed using a DNA microarray.

(b) Measurement Result

No change has been observed in the expression of NANOG, TDGF, GABRB3, DNMT3B, GDF3, POU5F1, FGF4, GAL, LEFT1, IFITM1, NODAL, TERT, UTF1, FOXD3, LEFT2, LIN28A, LIN28B, GRB7, PODXL, CD9, or BRIX1 as a known human ES cell marker gene (Non Patent Literature 4) specifically observed in undifferentiation, and further, little change has been observed in the expression of other general genes. This has also showed that the undifferentiation capability of stem cells is not changed even under long-term culture in the presence of "undifferentiated stem cell-specific labeled probe."

The above results have verified that the "undifferentiated stem cell-specific labeled probe" of the present invention has no cytotoxicity in stem cells.

4. Kit or Apparatus for Determining Differentiation Status of Stem Cell, Comprising "Undifferentiated Stem Cell-Specific Probe" of Present Invention The "undifferentiated stem cell-specific labeled probe" of the present invention can form a kit or an apparatus together with the following means (1) to (3) to make a kit or an apparatus for determining the differentiation status of stem cells.

(1) An undifferentiated stem cell-specific labeled probe in which BC2LCN lectin or a modified product thereof is labeled with a detectable labeling substance.

(2) A means for adding an undifferentiated stem cell-specific probe to the surface of stem cells, or a means for adding the probe to a solution containing the stem cells. For example, an automatic pipetting apparatus; however, the means is optional because the means can be replaced by a manual mean.

(3) A means or an apparatus for detecting a label. For example, when a fluorescence-labeled undifferentiated stem cell-specific labeled probe is used, it is a fluorescent microscope or a plate reader, and in the case of enzyme labeling or biotin labeling, it is an image analyzer or the like.

The undifferentiated stem cell-specific labeled probe of the present invention and the means or the apparatus for detecting a label can be made in a set to make a kit for determining the differentiation status of stem cells. In addition, they can be made in a set with the means for adding the undifferentiated stem cell-specific labeled probe to the cultured stem cells to automate the analysis of the undifferentiated stem cells. Here, the automation is preferably performed while maintaining the state of culturing stem cells.

5. Kit or Apparatus for Isolating Undifferentiated Stem Cell, Comprising "Undifferentiated Stem Cell-Specific Probe" of Present Invention A kit or an apparatus can be made together with the following means (1) to (3) to isolate only stem cells in an undifferentiated state.

(1) The undifferentiated stem cell-specific probe BC2LCN lectin or a modified product thereof (which may be labeled with a detectable labeling substance).

(2) A means for supplying the undifferentiated stem cell-specific probe into a culture medium of stem cells. For example, an automatic pipetting apparatus; however, the means is optional because the means can be replaced by a manual mean.

(3) A means or an apparatus for separating undifferentiated stem cells or differentiated cells. For example, a flow cytometry equipped with a cell sorter, or a magnetic cell separation apparatus.

The undifferentiated stem cell-specific probe of the present invention is made in a set with a means or an apparatus for separating the undifferentiated stem cells having bound to the undifferentiated stem cell-specific probe, and as a result, stem cells in a undifferentiated state can be separated and collected from cells whose differentiation is advanced; and therefore, not only stem cells in an undifferentiated state can be isolated, but also only cells whose differentiation is completely advanced can be isolated. In addition, a means for adding the undifferentiated stem cell-specific probe to the cultured stem cells can be made in a set therewith to automate the separation and collection of stem cells in an undifferentiated state or cells whose differentiation is advanced. Here, the automation is preferably performed while maintaining the state of culturing stem cells.

EXAMPLES

The present invention will be described below in detail with reference to Examples. However, the present invention is not intended to be limited thereto.

Other terms and concepts according to the present invention are based on the meanings of the terms idiomatically used in the art, and various techniques used for practicing the present invention can be easily and positively performed by one of ordinary skill in the art based on known literature and the like, particularly except for the techniques whose written sources are acknowledged. Various analyses and the like were performed in line with methods as described in the instruction manuals, catalogs, or the like of the analyzers, reagents, or kits used.

Reference shall be made as the contents of description of the present invention to the contents described in the technical references, patent publications, and patent application specifications cited herein.

Example 1

Cell Staining of Human ES Cell

Human ES cells (KhES-1 strain) used in this Example were obtained from Institute for Frontier Medical Sciences, Kyoto University. These cells were cultured by the method of Suemori et al. (see Non Patent Literature 6). ES cell colonies were fixed with 4% paraformaldehyde and washed with PBS, to which rBC2LCN lectin fluorescently labeled (bound to Cy3) was then added for reaction at room temperature for 1 hour (A in FIG. 1). As a target for comparison, the stained image of the ES cell colonies is shown which was reacted with Tra-1-60 antibody or anti-Nanog antibody specifically recognizing undifferentiated ES cells or iPS cells and then further reacted with anti-mouse IgM-Alexa 488 or anti-rabbit IgG-Alexa 594 as a secondary antibody (A in FIG. 1). The fluorescence-labeled rBC2LCN lectin strongly stained the ES cells as did Tra-1-60 antibody or anti-Nanog antibody. Because the above experiment was performed without crushing cells, it is noted that the sugar chain structure "Fucα1-2Galβ1-3GlcNAc/GalNAc" recognized by BC2LCN lectin as an antigen on the ES cell surface was recognized by the Tra-1-60 antibody was present as a constituent sugar of a glycoprotein or a glycolipid abundantly expressed on the surface of ES cells in an undifferentiated state so as to cover the cell surface.

In addition, ES cells were cultured by adding retinoic acid to a final concentration of $10^{-5}$ M according to the method of Draper et al. (see Non Patent Literature 7) for the induction of differentiation of the cells (B in FIG. 1). The culture was performed for 7 days to confirm that the differentiation had sufficiently advanced from the cell morphology, and the fluorescence-labeled rBC2LCN lectin was then reacted with the cells (B in FIG. 1). As a target for comparison, Tra-1-60 antibody or anti-Nanog antibody was reacted with the secondary antibody of each antibody (B in FIG. 1). In ES cells differentiated by retinoic acid treatment, the fluorescence of rBC2LCN lectin was little detected as was anti-Nanog antibody as an undifferentiation marker. In contrast, the intensity of fluorescence of the Tra-1-60 antibody as an undifferentiation marker remained to a sufficiently observable extent (B in FIG. 1).

These experimental results show that the sugar chain antigen recognized by Tra-1-60 antibody used as a known undifferentiation marker still maintains an appreciable expression level even in a state of advanced differentiation on the cell surface whereas the sugar chain structure "Fucα1-2Galβ1-3GlcNAc/GalNAc" recognized by BC2LCN lectin has been expressed so as to cover the cell surface in an undifferentiated state but is almost no longer expressed when differentiation advances. The above experiment also demonstrated that BC2LCN lectin had a highly excellent capability of detecting undifferentiated stem cells, comparable to that of anti-Nanog antibody. The antigen for anti-Nanog antibody is an intracellular protein, whereas the sugar chain structure recognized by BC2LCN lectin is present on the cell surface; thus, the lectin was demonstrated to be highly useful for an excellent kit for determining differentiation or undifferentiation, specifically recognizing stem cells having undifferentiated properties, such as ES cells.

Example 2

Figure 2:
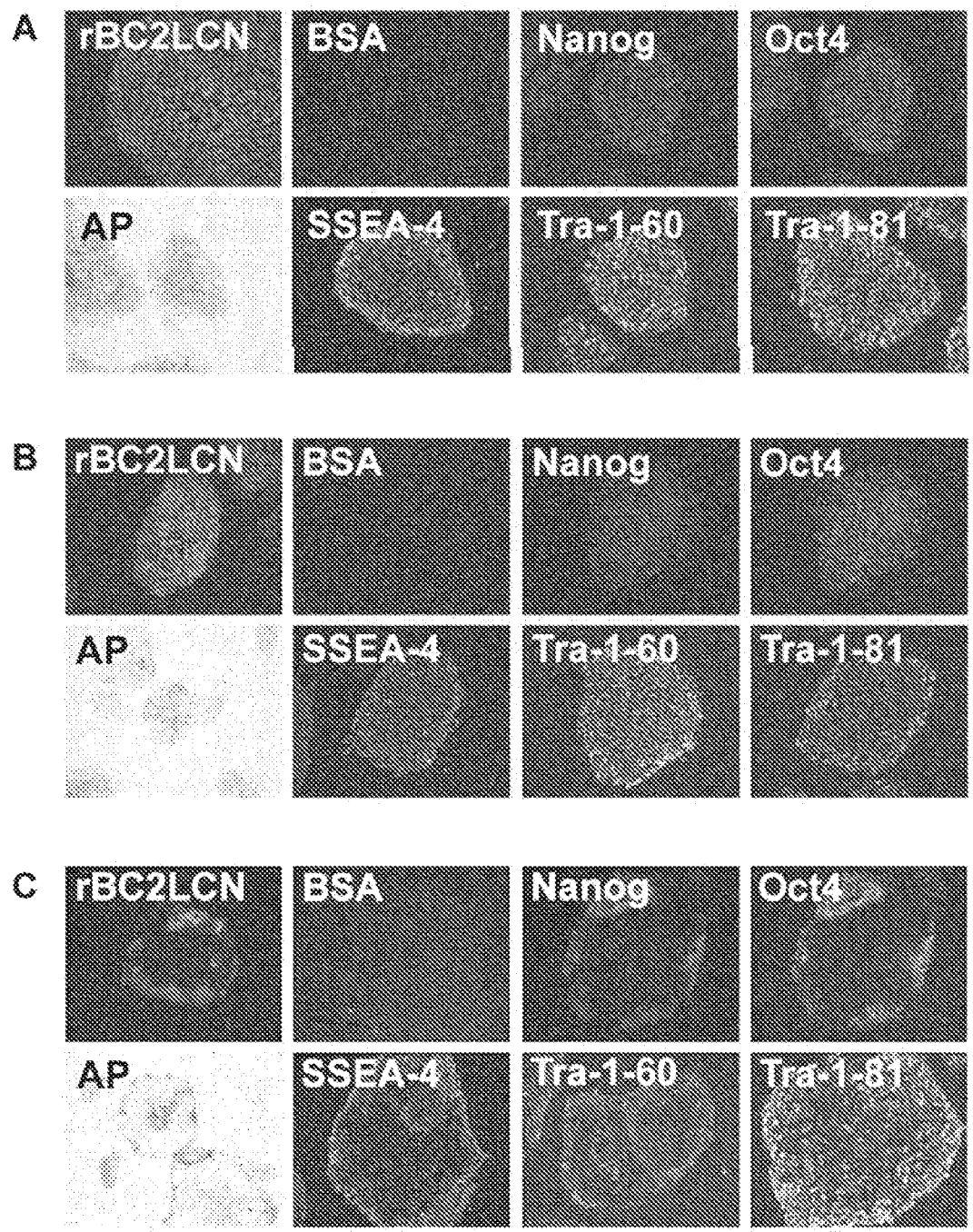
FIG. 2 is a series of photographs showing the results of staining undifferentiated iPS cells (253G1 strain) and iPS cells subjected to a differentiation induction treatment (retinoic acid treatment) with Cy3-labeled rBC2LCN lectin and known undifferentiation markers.

Staining of Human iPS Cell iPS cells (253G1 strain) used in this Example were obtained from the Riken BioResource Center. Cells were cultured by the method of Tateno et al. (see Non Patent Literature 1). Cells were fixed with 4% paraformaldehyde and washed with PBS, to which rBC2LCN lectin fluorescently labeled (bound to Cy3) was then added for reaction at room temperature for 1 hour (FIG. 2). Fluorescence-labeled BSA was used as a negative control (FIG. 2). As a target for comparison, staining with alkaline phosphatase as a marker for undifferentiated ES cells or iPS cells or staining with an antibody (anti-Nanog antibody, anti-Oct3/4 antibody, SSEA-4 antibody, Tra-1-60 antibody, or Tra-1-81 antibody) was performed (FIG. 2). It was shown that fluorescence-labeled BC2LCN lectin strongly stained undifferentiated iPS cells and strongly detected iPS cells to the same extent as or more extent than staining with AP as a known undifferentiation marker and various antibody staining (A in FIG. 2).

iPS cells were cultured by adding retinoic acid to a final concentration of $10^{-5}$ M according to the method of Draper et al. (see Non Patent Literature 7) for the induction of differentiation of the cells. After culturing the cells for 5 days and confirming the commencement of differentiation from the cell morphology, fluorescence-labeled rBC2LCN lectin was reacted with the cells (C in FIG. 2). As target cells for comparison, the cells cultured for 5 days without adding retinoic acid were used (B in FIG. 2). Staining with AP as a marker for undifferentiated ES cells or iPS cells and staining with an antibody (anti-Nanog antibody, anti-Oct3/4 antibody, SSEA-4 antibody, Tra-1-60 antibody, or Tra-1-81 antibody) were performed. For the iPS cell strain differentiated by retinoic acid treatment, the fluorescence reaction of rBC2LCN lectin was observed in anti-Nanog antibody- or anti-Oct3/4 antibody-positive cells maintaining their undifferentiated properties around each iPS cell colony, but not detected in anti-Nanog antibody- or anti-Oct3/4 antibody-negative cells losing their undifferentiated properties in the center of the colony (C in FIG. 2). In contrast, the intensity of the fluorescence of Tra-1-60 antibody or Tra-1-81 antibody remained to a sufficiently observable extent even in the anti-Nanog antibody- or anti-Oct3/4 antibody-negative cells losing their undifferentiated properties in the center of the colony (C in FIG. 2).

The above experiment demonstrated that BC2LCN lectin had a highly excellent capability of detecting undifferentiated stem cells comparable to that of anti-Nanog antibody or anti-Oct3/4 antibody as an undifferentiation sugar chain marker for determining differentiation or undifferentiation. BC2LCN lectin was shown to be highly useful as an excellent reagent for determining differentiation or undifferentiation, specifically recognizing stem cells, such as iPS cells, having undifferentiated properties.

Example 3

Figure 3:
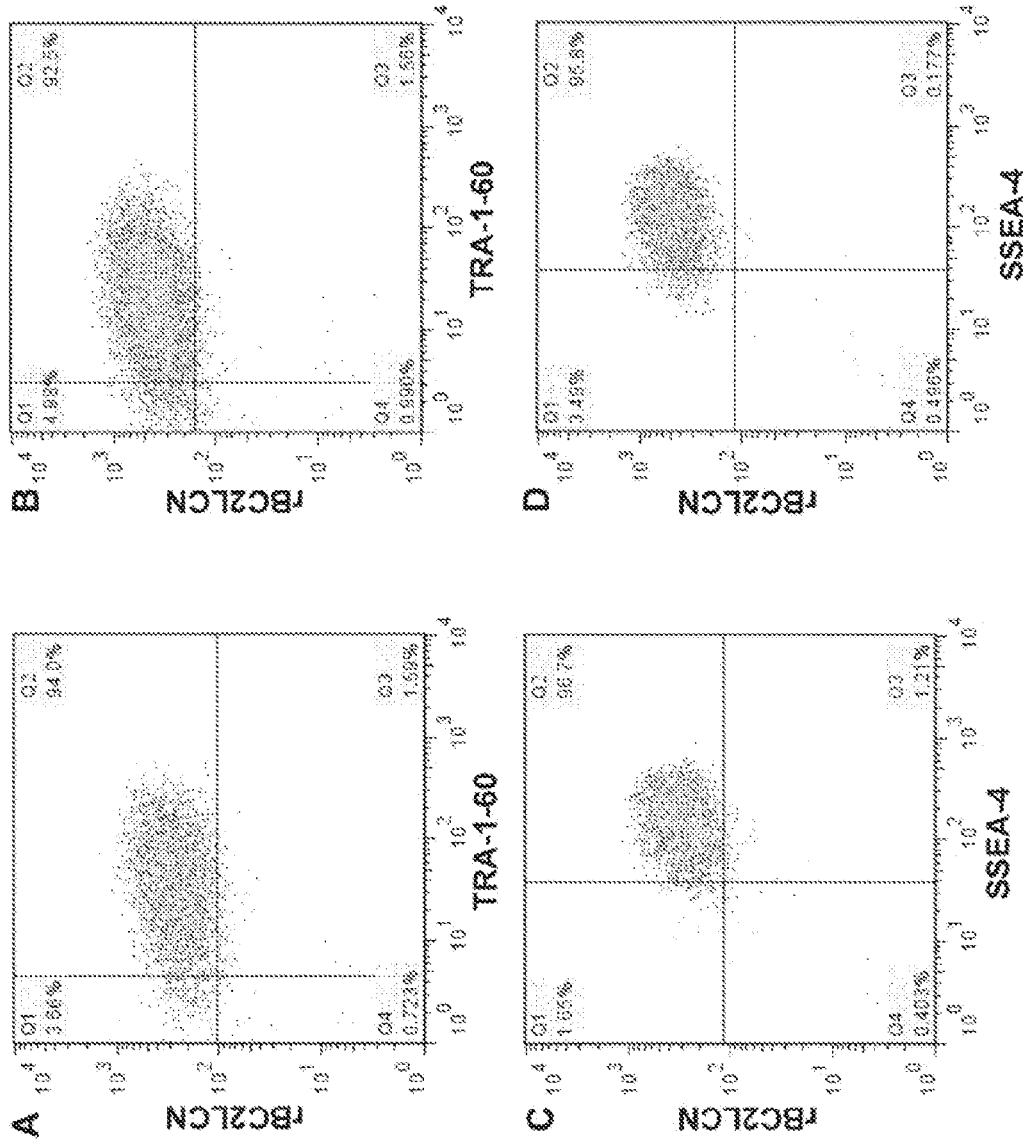
FIG. 3 is a series of graphs showing the results of analyzing undifferentiated iPS cells (253G1 strain) by a flow cytometry method using fluorescence-labeled rBC2LCN lectin and Tra-1-60 antibody or SSEA-4 antibody.

Flow Cytometry of iPS Cell Using Fluorescence-Labeled BC2LCN Lectin iPS cells (253G1 strain) prepared in the same way as in Example 2 were dissociated by enzyme treatment, reacted with fluorescence-labeled (HiLyte Fluor 647-bound) rBC2LCN lectin and a known undifferentiation detection antibody (Tra-1-60 antibody or SSEA-4 antibody), and subjected to flow cytometry analysis using a FACS apparatus (FIG. 3).

As a result, 92.5 to 94.0% of all cells simultaneously bound to Tra-1-60 antibody and rBC2LCN lectin (A and B in FIG. 3). In addition, 95.8 to 96.7% of all cells simultaneously bound to SSEA-4 antibody and rBC2LCN lectin (C and D in FIG. 3). These results demonstrate that BC2LCN lectin can effectively sort iPS cells maintaining undifferentiation.

No difference was observed in the percentage of cells simultaneously binding to rBC2LCN and Tra-1-60 antibody or SSEA-4 antibody between a case where cells were reacted first with rBC2LCN lectin and later with Tra-1-60 antibody or SSEA-4 antibody (A or C in FIG. 3) and a case where cells were reacted first with Tra-1-60 antibody or SSEA-4 antibody and later with rBC2LCN lectin (B or D in FIG. 3). This shows that BC2LCN does not inhibit binding to the known undifferentiation detection antibody (Tra-1-60 antibody or SSEA-4 antibody) and both can be combined to improve undifferentiation detection sensitivity.

This property can be utilized to separate and collect cells alive by the flow cytometry method; thus, it is also possible to remove undesired contaminated differentiated cells in storing stem cells such as ES cells and iPS cells or in attempting to proliferate them while maintaining undifferentiated properties. The property can also be utilized to remove cells remaining while maintaining undifferentiated properties by the flow cytometry method when various organ cells (heart muscle cells, liver cells, neuronal cells, pancreatic islet cells, chondrocytic cells, bone cells, and the like) have been prepared from stem cells such as ES cells and iPS cells.

Example 4

Staining of Human ES Cell and iPS Cell

Human ES cells (KhES-3 strain) used in this Example were obtained from the Institute for Frontier Medical Sciences, Kyoto University. These cells were cultured by the method of Suemori et al. (see Non Patent Literature 6).

Human iPS cells (201B7 strain) used in this Example were obtained from the Riken BioResource Center. Cells were cultured by the method of Tateno et al. (see Non Patent Literature 1).

ES cells and iPS cells were fixed with 4% paraformaldehyde and washed with PBS, to which rBC2LCN lectin fluorescently labeled (bound to Cy3) was then added for reaction at room temperature for 1 hour. It was shown that fluorescence-labeled rBC2LCN lectin strongly stained KhES-3 strain and 201B7 strain and detected a large variety of human ES cells and iPS cells (FIG. 4).

Figure 4:
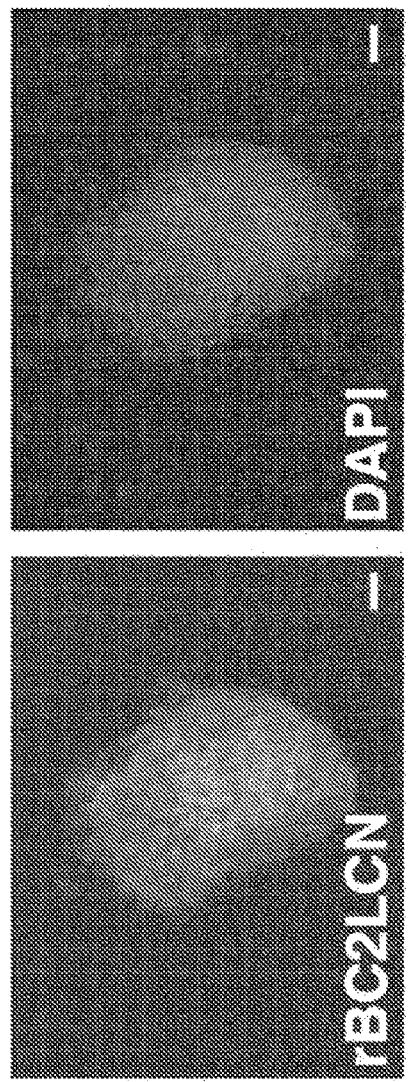
FIG. 4 is a series of photographs showing the results of staining undifferentiated ES cells (KhES-3 strain) and undifferentiated iPS cells (201B7 strain) with Cy3-labeled rBC2LCN lectin.
Figure 4:
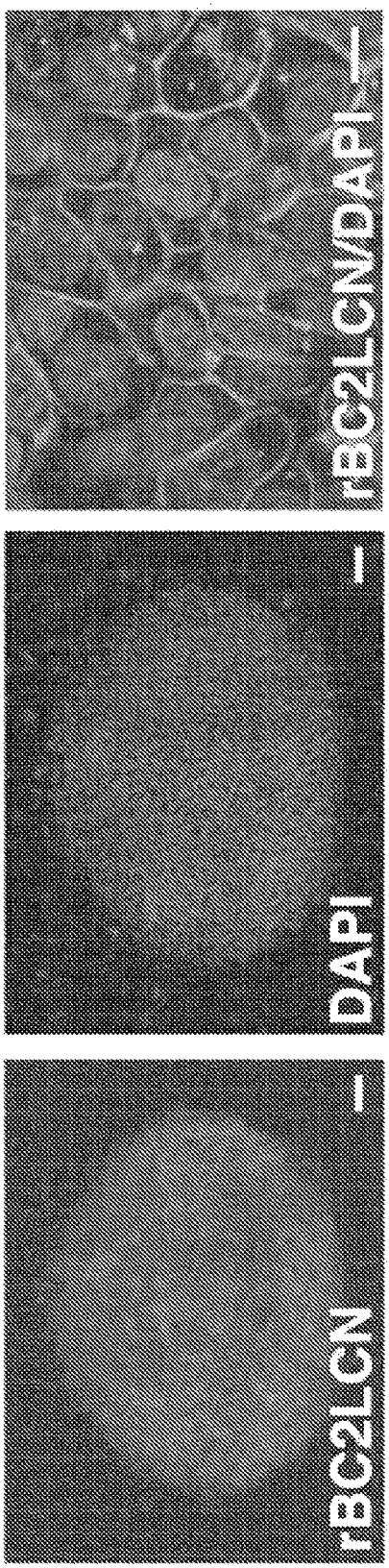

Observation using a confocal fluorescence microscope confirmed that the fluorescence-labeled rBC2LCN lectin stained the cell membrane of 201B7 strain (B (right) in FIG. 4). This demonstrates that the sugar chain structure "Fucα1-2Galβ1-3GlcNAc/GalNAc" recognized by BC2LCN lectin is present as a constituent sugar of a glycoprotein and a glycolipid abundantly expressed on the surface of iPS cells in an undifferentiated state so as to cover the cell surface. Because the sugar chain structure recognized by BC2LCN lectin was present on the cell surface, the lectin was demonstrated to be highly useful for an excellent kit for determining differentiation or undifferentiation, specifically recognizing stem cells, such as ES cells, having undifferentiated properties.

Example 5

Flow Cytometry of iPS Cell and ES Cell Using Fluorescence-Labeled BC2LCN Lectin ES cells (KhES-1 strain) prepared in the same way as in Example 1, iPS cells (253G1 strain) prepared in the same way as in Example 2, and human dermal fibroblasts (HDF) prepared by a method recommended by ATCC (http://www.atcc.org/attachments/13049.pdf) were dissociated by enzyme treatment and reacted with fluorescence-labeled (HiLyte Fluor 647-bound) rBC2LCN lectin. As a result of flow cytometry analysis, ES cells and iPS cells bound to rBC2LCN lectin, and marked shift in a fluorescence peak was observed, but no binding to HDF was observed (A to C in FIG. 5).

Figure 5:
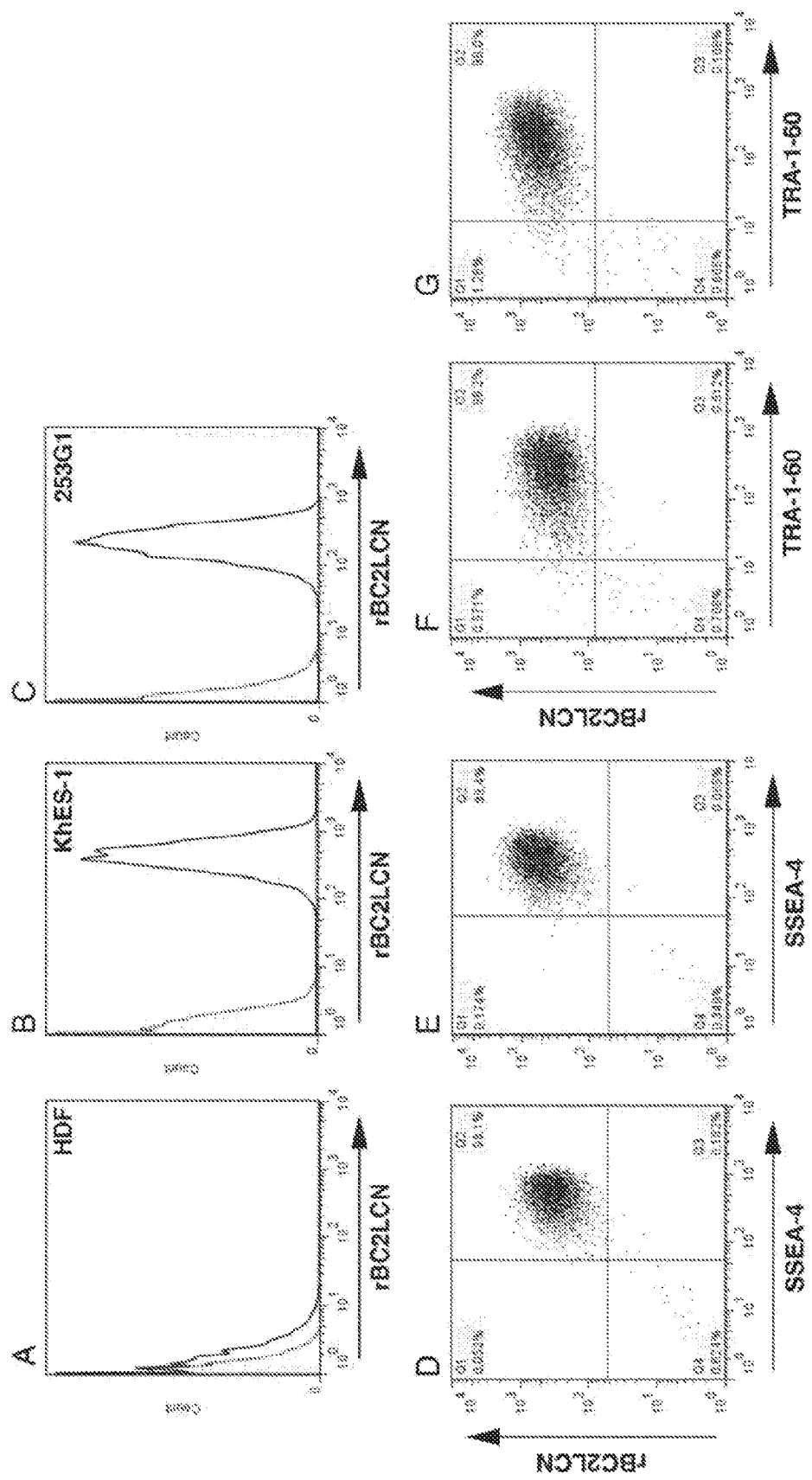
FIG. 5 is a series of graphs showing the results of analyzing fibroblasts (HDF strain), undifferentiated ES cells (KhES-1 strain), and undifferentiated iPS cells (253G1 strain) by a flow cytometry method using fluorescence-labeled rBC2LCN lectin and Tra-1-60 antibody or SSEA-4 antibody.

In addition, ES cells (KhES-1 strain) were reacted with fluorescence-labeled (HiLyte Fluor 647-bound) rBC2LCN lectin and a known undifferentiation detection antibody (SSEA-4 antibody or Tra-1-60 antibody) to perform flow cytometry analysis using a FACS apparatus (D to G in FIG. 5). As a result, 99.1 to 99.4% of all cells simultaneously bound to SSEA-4 antibody and rBC2LCN lectin (D and E in FIG. 5). In addition, 98.0 to 98.2% of all cells simultaneously bound to Tra-1-60 antibody and rBC2LCN lectin (F and G in FIG. 5). These results demonstrate that BC2LCN lectin can effectively sort iPS cells maintaining undifferentiation.

No difference was observed in the percentage of cells simultaneously binding to rBC2LCN and SSEA-4 antibody or Tra-1-60 antibody between a case where cells were reacted first with rBC2LCN lectin and later with SSEA-4 antibody or Tra-1-60 antibody (D or F in FIG. 5) and a case where cells were reacted first with SSEA-4 antibody or Tra-1-60 antibody and later with rBC2LCN lectin (E or G in FIG. 5). This shows that BC2LCN does not inhibit binding to the known undifferentiation detection antibody (SSEA-4 antibody or Tra-1-60 antibody) and both can be combined to improve undifferentiation detection sensitivity.

This property can be utilized to separate and collect cells alive by the flow cytometry method; thus, it is also possible to remove undesired contaminated differentiated cells in storing stem cells such as ES cells and iPS cells or in attempting to proliferate them while maintaining undifferentiated properties. The property can also be utilized to remove cells remaining while maintaining undifferentiated properties by the flow cytometry method when various organ cells (heart muscle cells, liver cells, neuronal cells, pancreatic islet cells, chondrocytic cells, bone cells, and the like) have been prepared from stem cells such as ES cells and iPS cells.

Example 6

Separation of Tumorigenic Cell Using Flow Cytometry Method

Figure 6:
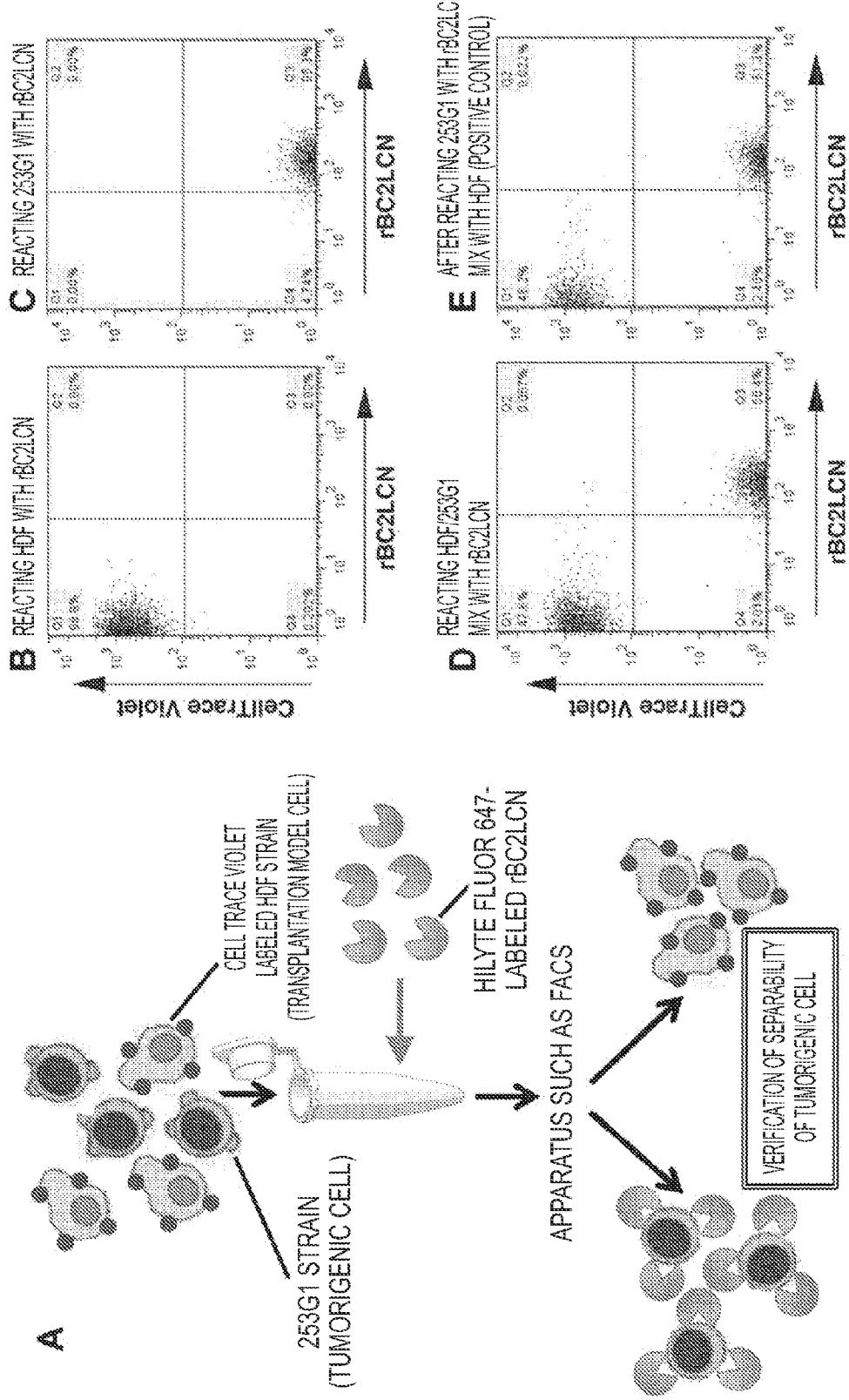
FIG. 6 is a series of drawings showing the results of verifying whether or not only tumorigenic cells can be separated from fibroblasts (HDF strain) and undifferentiated iPS cells (=tumorigenic cells (2531 strain)) mixed in advance, using rBC2LCN.

Human dermal fibroblasts (HDF) prepared in the same way as in Example 5 were dissociated by enzyme treatment, labeled using CellTrace Violet Cell Proliferation Kit (Invitrogen Corporation), and used as a model of cells for transplantation (transplantation model cells). iPS cells (253G1 strain) as tumorigenic cells prepared in the same way as in Example 2 were mixed with the transplantation model cells HDF in a mixing ratio of 1:1, which was then reacted with fluorescence-labeled (HiLyte Fluor 647-bound) rBC2LCN lectin (A in FIG. 6). As a result of flow cytometry analysis, iPS cells bound to rBC2LCN lectin, and the transplantation model cells HDF did not bind to rBC2LCN lectin; thus, separation occurred at percentages of 50.4% and 46.7% which are almost the same as the original mixing ratio (1:1) (D in FIG. 6). These percentages were almost the same as the results of mixing iPS cells bound to rBC2LCN lectin in advance with the transplantation model cells HDF at a cell number ratio of 1:1 and performing flow cytometry analysis (E in FIG. 6). When only the transplantation model cells HDF were reacted with rBC2LCN lectin, all of the cells did not bind to rBC2LCN lectin (B in FIG. 6), and when only iPS cells were reacted with rBC2LCN lectin, 95.3% of the cells bound to rBC2LCN lectin (C in FIG. 6).

These results demonstrate that BC2LCN lectin can effectively sort iPS cells maintaining undifferentiation. This property can be utilized to separate and collect cells alive by the flow cytometry method; thus, it is also possible to remove undesired contaminated differentiated cells in storing stem cells such as ES cells and iPS cells or in attempting to proliferate them while maintaining undifferentiated properties. The property can also be utilized to remove cells remaining while maintaining undifferentiated properties by the flow cytometry method when various organ cells (heart muscle cells, liver cells, neuronal cells, pancreatic islet cells, chondrocytic cells, bone cells, and the like) have been prepared from stem cells such as ES cells and iPS cells.

Example 7

Measurement of Strength of Binding of BC2LCN Lectin to Stem Cell

Figure 7:
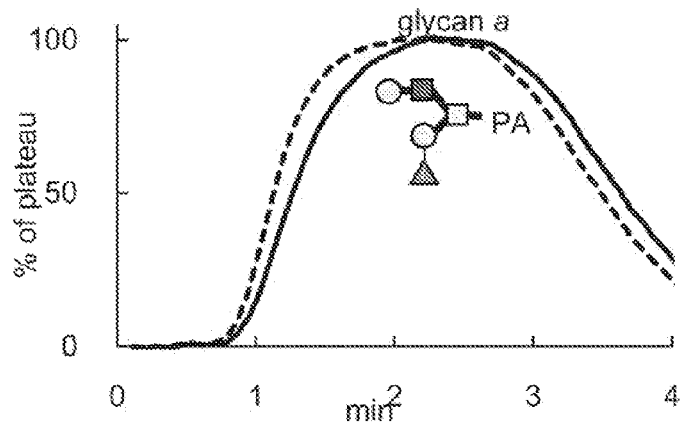
FIG. 7 is a pair of graphs showing the results of measuring the binding strength between undifferentiated ES cells (H1 strain (WA01 strain)) and rBC2LCN using a flow cytometry method.
Figure 7:
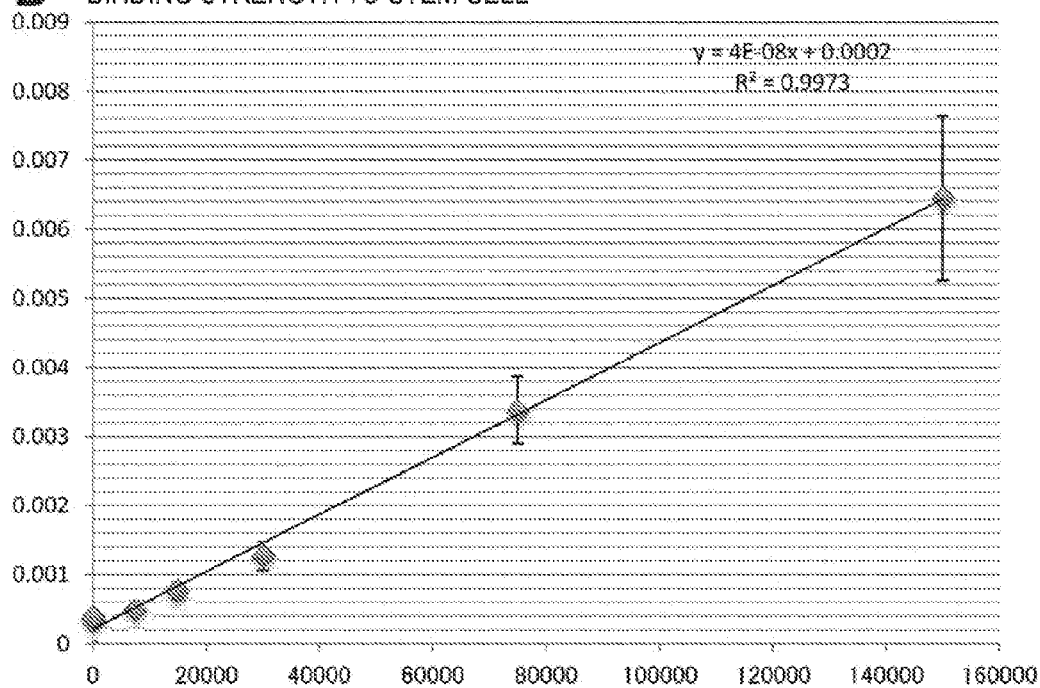

Human ES cells (H1 strain (WA01 strain)) used in this Example were obtained from the Wisconsin International Stem Cell (WISC) Bank. The culture method was according to the protocol of WiCell Research Institute, Inc. Solutions of fluorescence-labeled (HiLyte Fluor 647-bound) rBC2LCN lectin in a dilution series (0.01, 0.005, 0.002, 0.001, 0.0005, 0.0002, and 0.0001 mg/ml) were prepared and reacted with human ES cells (H1 strain (WA01 strain)) dissociated by enzyme treatment. When the results of flow cytometry analysis were reciprocally plotted to calculate the Michaelis constant, which is considered to be an approximate value for the dissociation constant, the value of Kd=2.0.E−07 was obtained (B in FIG. 7). When the binding strength between BC2LCN lectin and "Fucα1-2Galβ1-3GlcNAc/GalNAc" as its target sugar chain was measured by frontal affinity chromatography, the dissociation constant was Kd=4.0.E−0.5 (A in FIG. 7) (PCT/JP2012/006983), showing that BC2LCN had extremely high binding strength to undifferentiated stem cells.

Example 8

Toxicity Test of, and Vital Staining with, BC2LCN Lectin Using Stem Cell

Figure 8:
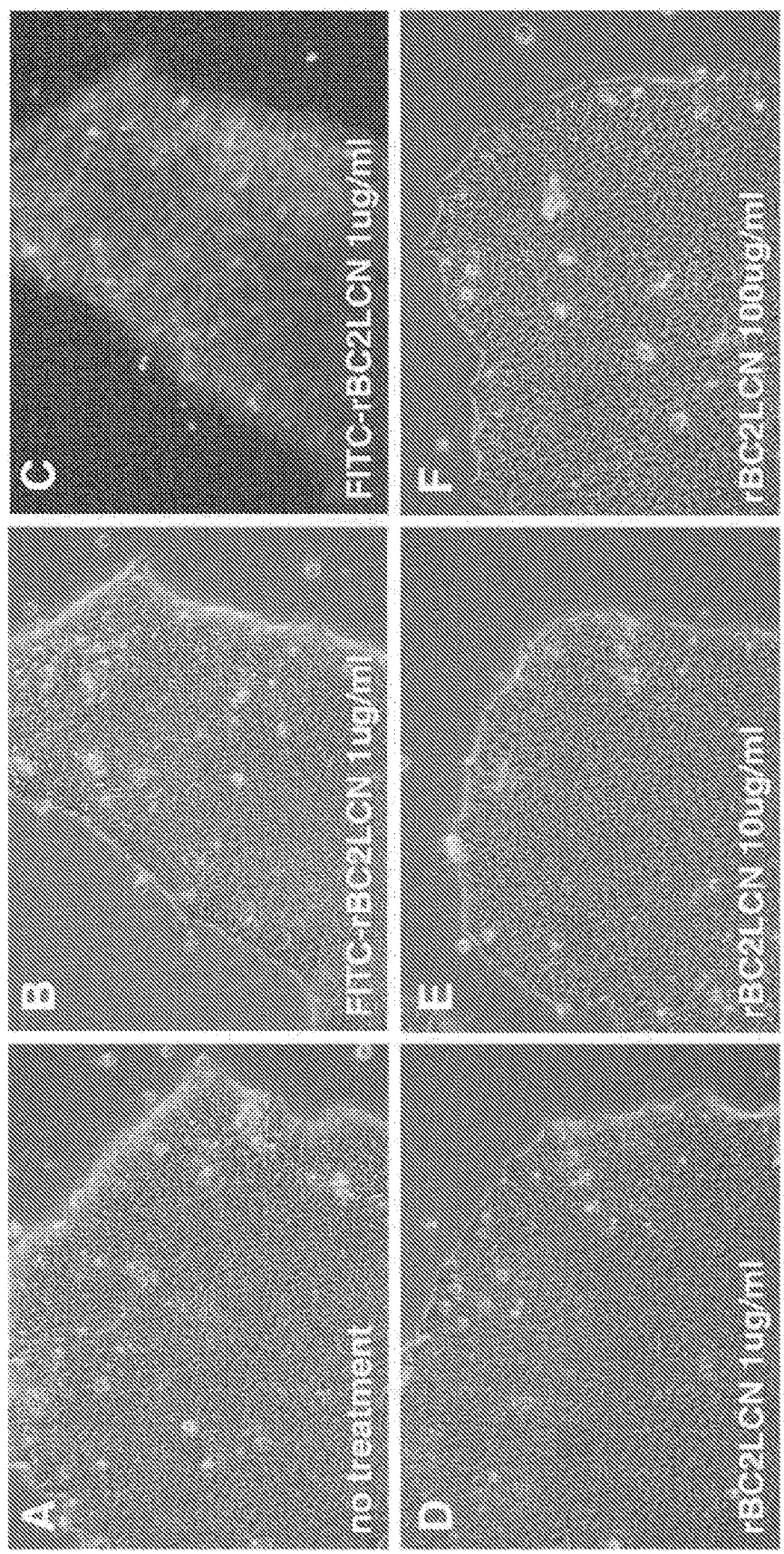
FIG. 8 is a series of photographs showing the results of adding a high concentration of rBC2LCN to undifferentiated ES cells (H1 strain (WA01 strain)) to observe cell proliferation and colony morphology. Undifferentiated ES cells (H1 strain (WA01 strain)) were also stained alive with FITC-labeled rBC2LCN.

Human ES cells (H1 strain (WA01 strain)) used in this Example were prepared in the same way as in Example 7. rBC2LCN or FITC-bound rBC2LCN was added in daily replacing the medium for 3 days from the day following passage, and the proliferative activity of ES cells was measured by the morphological observation of colonies at day 4 of culture (FIG. 8). The observed morphology was the same as that of untreated colonies (A in FIG. 8) under all conditions of the addition of rBC2LCN at concentrations of 1, 10, 100 µg/ml (D to F in FIG. 8) and the addition of FITC-bound rBC2LCN at a concentration of 1 µg/ml (B in FIG. 8). This showed that the proliferative activity of ES cells was maintained even under long-term culture in the presence of BC2LCN, confirming that BC2LCN had no cytotoxicity.

When the colonies of B in FIG. 8 were subjected to fluorescent observation, a fluorescence signal was shown to be obtained in a state in which cells are alive (C in FIG. 8). This confirmed that fluorescence-labeled BC2LCN bound to human stem cells without showing toxicity and was effective as a non-invasive tool for determining properties of stem cells.

Example 9

Toxicity Test of BC2LCN Lectin Using Stem Cell

Figure 9:
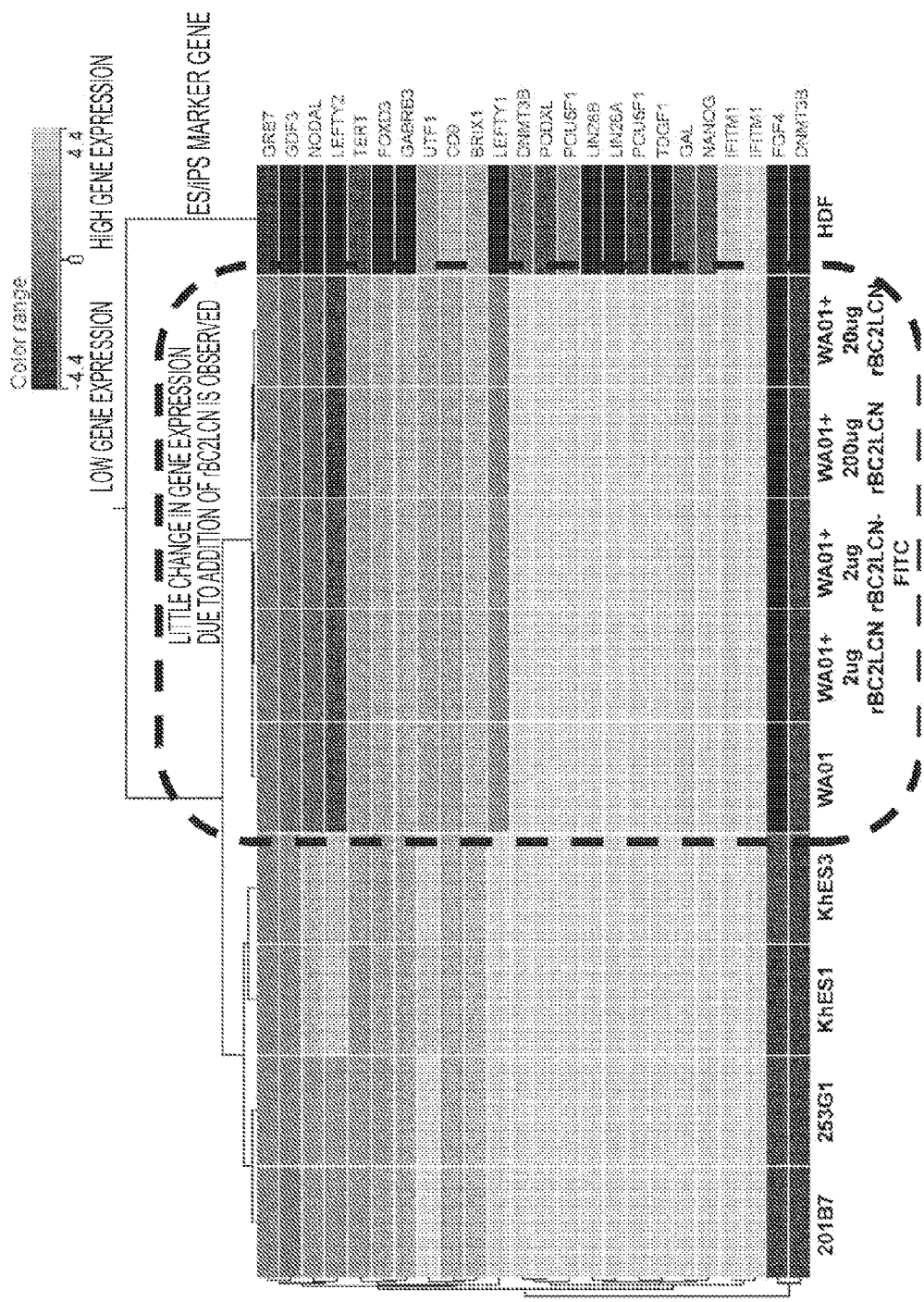
FIG. 9 is a diagram showing the results of the expression analysis of marker genes showing undifferentiated properties of ES cells by adding a high concentration of rBC2LCN to undifferentiated ES cells (H1 strain (WA01 strain)).

RNA was extracted from colonies under various treatment conditions obtained in Example 8 and subjected to exhaustive gene expression analysis using SurePrint G3 Human GE Microarray kit 8×60K (Agilent G4851A) from Agilent Technologies, Inc. RNAs of human ES cells (KhES-1 strain and KhES-3 strain), human iPS cells (201B7 strain and 253G1 strain), and human fibroblasts (HDF strain) prepared by the methods in Example 1, 2, 4, and 5 were similarly subjected to gene expression analysis. The expression of NANOG, TDGF, GABRB3, DNMT3B, GDF3, POU5F1, FGF4, GAL, LEFT1, IFITM1, NODAL, TERT, UTF1, FOXD3, LEFT2, LIN28A, LIN28B, GRB7, PODXL, CD9, and BRIX1 as known human ES cell marker genes (Non Patent Literature 4) specifically observed during undifferentiation was analyzed using Gene-Spring GX12.0 software from Agilent Technologies, Inc.; as a result, no difference was observed between the ES cells obtained from A, B, D, E, and F in FIG. 8 (FIG. 9). This showed that the undifferentiation capability of stem cells was not changed even under long-term culture in the presence of BC2LCN.

Example 10

Toxicity Test of BC2LCN Lectin Using Stem Cell

Figure 10:
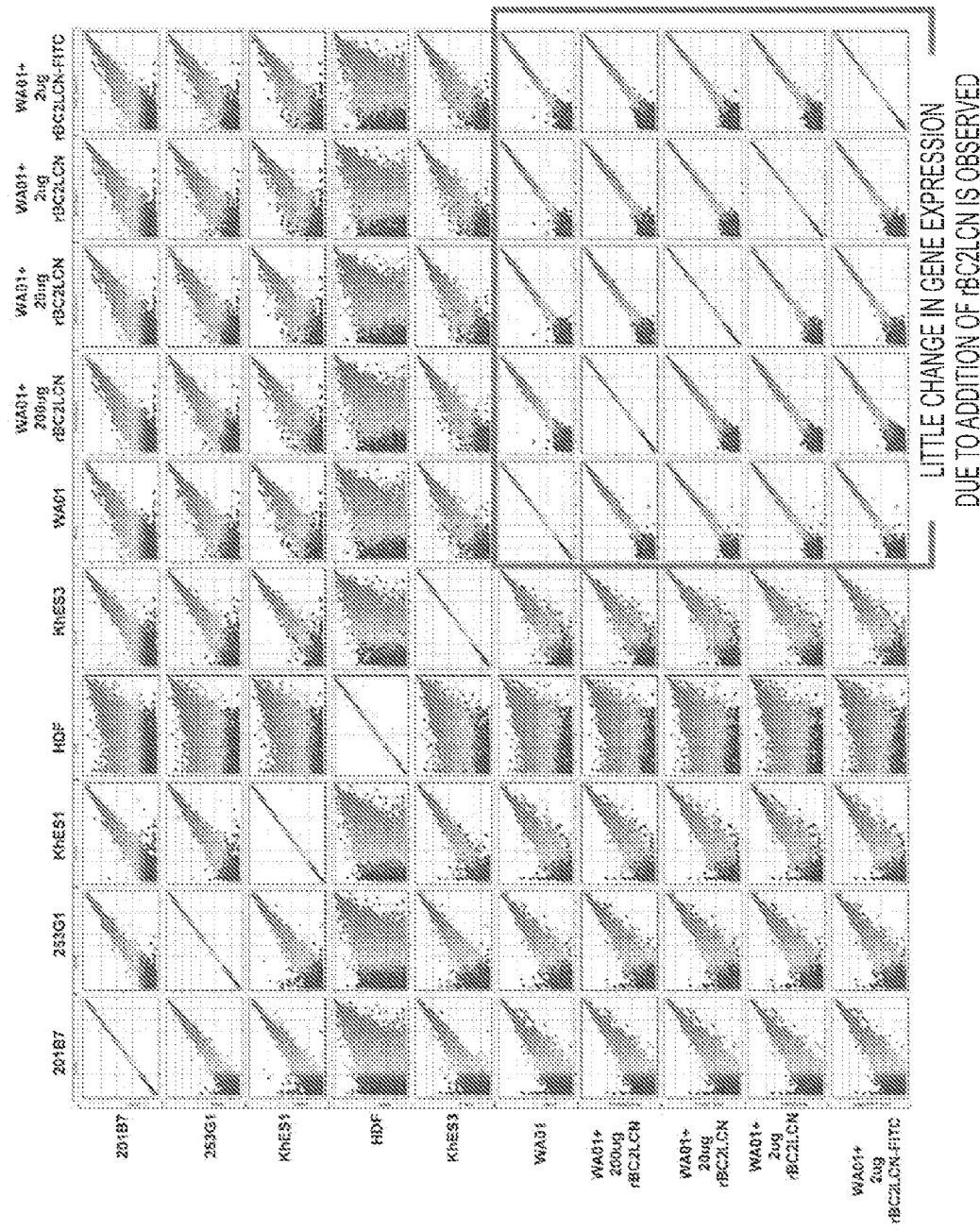
FIG. 10 is a diagram showing the results of exhaustive expression comparison of all of the genes for each condition by adding a high concentration of rBC2LCN to undifferentiated ES cells (H1 strain (WA01 strain)).

Using the DNA microarray data obtained in Example 9, the correlation of the expression pattern of the human total genes was analyzed between samples. As a result, little difference was observed in the expression level of not only the human ES cell marker genes but also the total genes between the ES cells obtained from A, B, D, E, and F in FIG. 8 (FIG. 10). This showed that the properties of stem cells were not changed even under long-term culture in the presence of BC2LCN.

Example 11

Toxicity Test of, and Vital Staining with, BC2LCN Lectin Using Stem Cell

Figure 11:
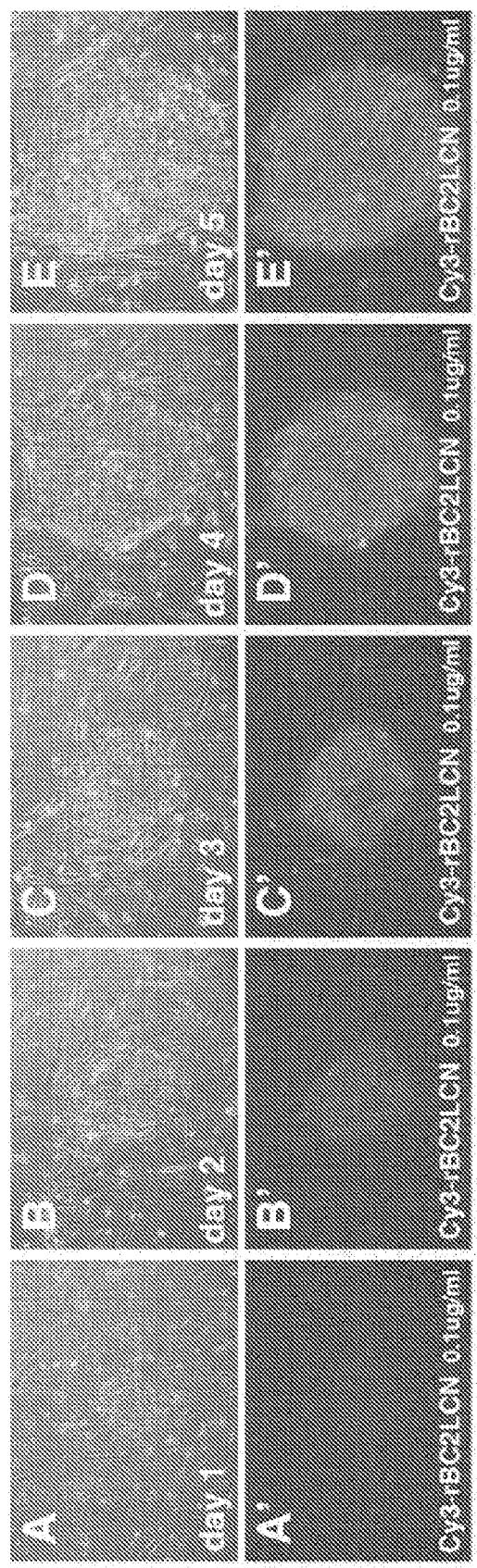
FIG. 11 is a series of photographs showing the results of staining undifferentiated iPS cells (201B7 strain) alive with Cy3-labeled rBC2LCN.

Human iPS cells (201B7 strain) used in this Example were obtained from the Riken BioResource Center. Cells were cultured by the method of Tateno et al. (see Non Patent Literature 1). In daily replacing the medium for 5 days from the day following passage, Cy3-bound rBC2LCN was added at a concentration of 0.1 µg/ml, and 2 hours later, photography was performed without medium replacement to verify the presence of the proliferation and vital staining of iPS cells (FIG. 11). As a result, as far as determination was performed using phase contrast microscopic images, no reduction in the cell proliferative capacity or toxicity in cells was observed (A to E in FIG. 11). This showed that the proliferative activity of iPS cells was maintained even under long-term culture in the presence of BC2LCN, confirming that BC2LCN had no cytotoxicity.

When the colonies of A to E in FIG. 11 were subjected to fluorescent observation, fluorescence signals were shown to be obtained in a state in which cells are alive (A' to E' in FIG. 11). This confirmed that fluorescence-labeled BC2LCN bound to human stem cells without showing toxicity and was effective as a non-invasive tool for determining properties of stem cells.

Example 12

Staining of Various Cells Differentiated from iPS Cell iPS cells (201B7 strain) used in this Example were obtained from the Riken BioResource Center. To obtain cells differentiated into 3 germ layers, an embryoid body (EB) was prepared. EB was prepared by the method of Takahashi et al. (see Non Patent Literature 8). EB was fixed with 4% paraformaldehyde, washed with PBS, and then simultaneously stained with Cy3-labeled rBC2LCN lectin and an antibody to each differentiation marker.

Figure 12:
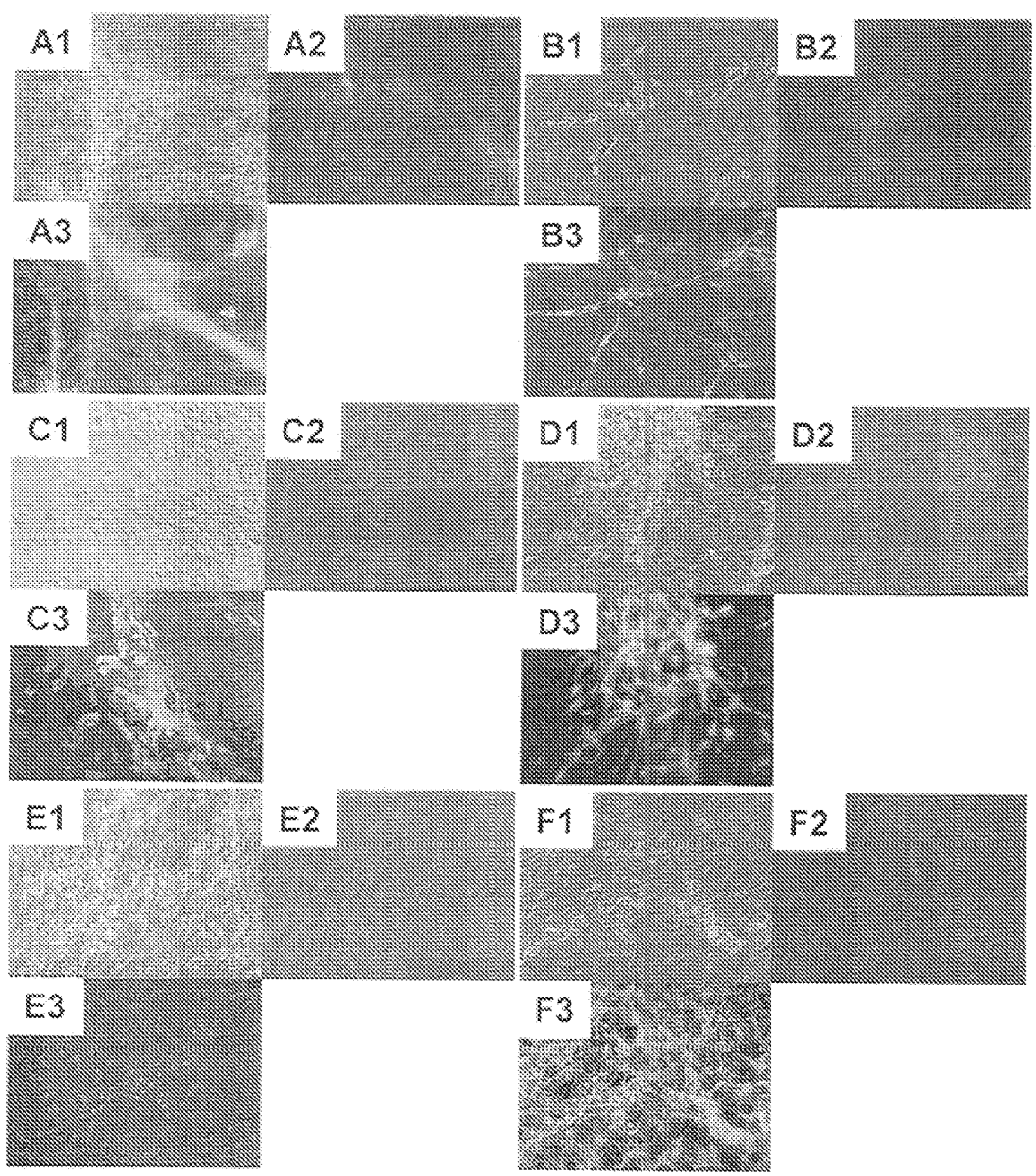
FIG. 12 is a diagram showing the results of staining cells differentiated from iPS cells with Cy3-labeled rBC2LCN.

The results are shown in FIG. 12. A and B show observation images of ectoderm cells; C and D, the images of mesoderm cells; E, the images of endoderm cells; and F, the images of mesoderm cells and endoderm cells. A1 to F1 show phase contrast microscopic images and A2 to F2 show images of fluorescent staining by rBC2LCN lectin. A3 to F3 show images of fluorescent staining by the antibodies to differentiation markers. Tuj1 (ectoderm marker) was used for A3; GFAP (ditto), for B3; a-SMA (mesoderm marker), for C3; Desmin (ditto), for D3; AFP (endoderm marker), for E3; and Vimentin (mesoderm and endoderm marker), for F3.

The staining by the antibodies to the differentiation markers confirmed that iPS cells differentiated into 3 germ layers in EB (see A3 to F3). On the other hand, no positive images were observed for the staining by rBC2LCN (see A2 to F2). These results showed that BC2LCN did not stain differentiated cells.

Example 13

Staining of Various Cells Differentiated from ES Cell

Human ES cells (H1 strain (WA01 strain)) used in this Example were obtained from the Wisconsin International Stem Cell (WISC) Bank. An embryoid body (EB) was prepared by the above-described method and simultaneously stained with Cy3-labeled rBC2LCN lectin and an antibody to each differentiation marker.

Figure 13:
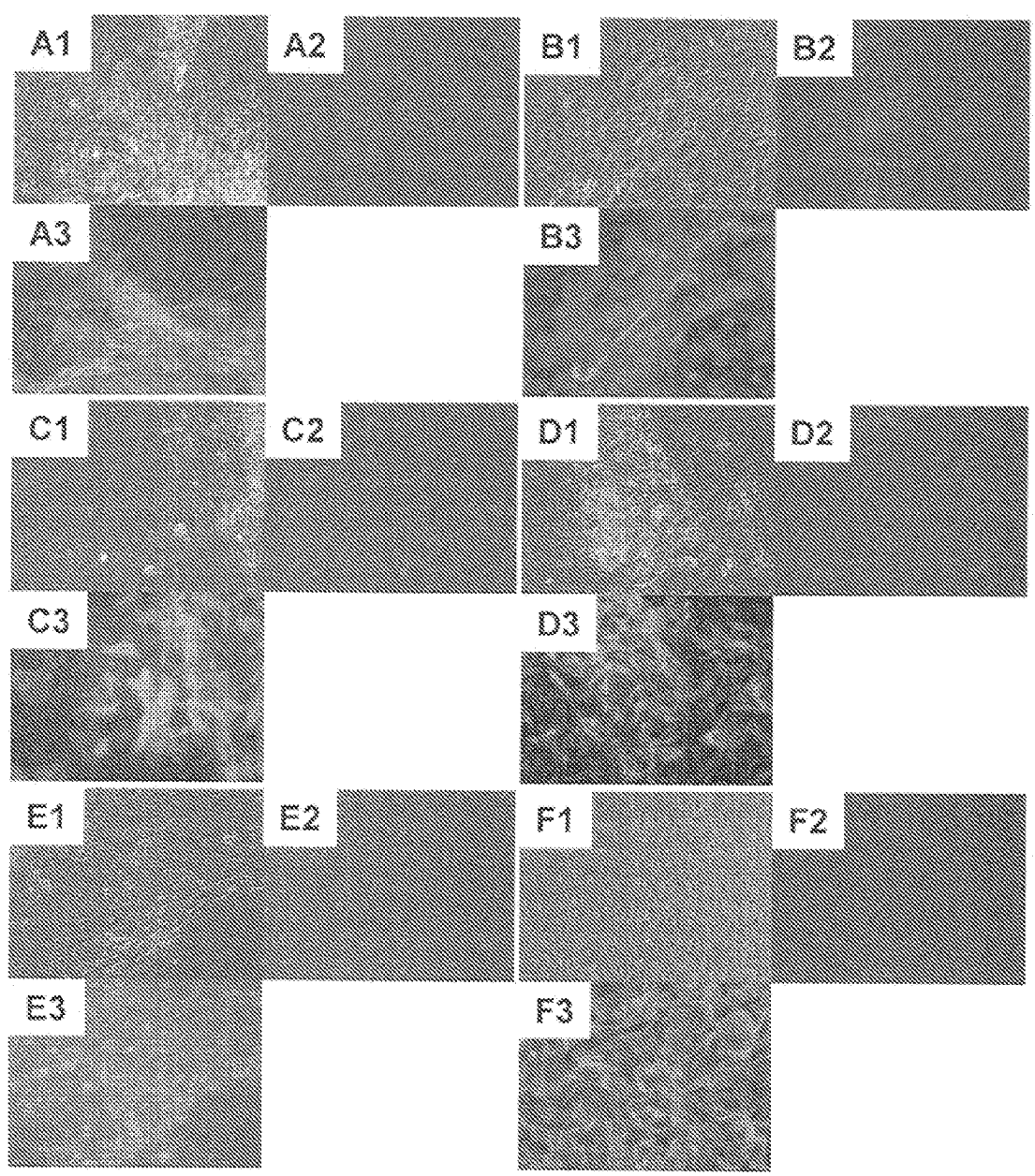
FIG. 13 is a diagram showing the results of staining cells differentiated from ES cells with Cy3-labeled rBC2LCN.

The results are shown in FIG. 13. A and B show observation images of ectoderm cells; C and D, the images of mesoderm cells; E, the images of endoderm cells; and F, the images of mesoderm cells and endoderm cells. A1 to F1 show phase contrast microscopic images and A2 to F2 show images of fluorescent staining by rBC2LCN lectin. A3 to F3 show images of fluorescent staining by the antibodies to differentiation markers. Tuj1 (ectoderm marker) was used for A3; GFAP (ditto), for B3; a-SMA (mesoderm marker), for C3; Desmin (ditto), for D3; AFP (endoderm marker), for E3; and Vimentin (mesoderm and endoderm marker), for F3.

The staining by the antibodies to the differentiation markers confirmed that ES cells differentiated into 3 germ layers in EB (see A3 to F3). On the other hand, no positive images were observed for the staining by rBC2LCN (see A2 to F2). These results showed that BC2LCN did not stain differentiated cells.

Reference to a "Sequence Listing," a Table, or a Computer Program Listing Appendix Submitted as an ASCII Text File The material in the ASCII text file, named "OHNO4-52848-seq-project-revised-2014-11-30_ST25.txt," created Nov. 30, 2014, file size of 4,096 bytes, is hereby incorporated by reference.

---

The invention claimed is:

1. A method for determining differentiation of a cell comprising:
   a step of contacting a test cell with a probe comprising a protein (A) or (B) below and
   a step of detecting the presence of binding of the probe to the test cell:
   (A) a protein comprising an amino acid sequence shown in SEQ ID NO: 1 and recognizing a sugar chain structure of "Fucα1-2Galβ1-3GlcNAc" and/or "Fucα1-2Galβ1-3GlcNAc;" and
   (B) a protein comprising an amino acid sequence in which one or two amino acids in the amino acid sequence shown in SEQ ID NO: 1 are deleted, substituted, inserted, or added, and recognizing a sugar chain structure of "Fucα1-2Galβ1-3GlcNAc" and/or "Fucα1-2Galβ1-3GalNAc;"
   wherein binding of the probe to the test cell indicates an undifferentiated state.

2. The method for determining differentiation of a cell according to claim 1, wherein the test cell is an undifferentiated stem cell or a stem cell subjected to a differentiation induction treatment.

3. The method for determining differentiation of a cell according to claim 2, wherein the undifferentiated stem cell is a stem cell treated for the maintenance of an undifferentiated state or a somatic cell subjected to pluripotency induction treatment.

4. The method for determining differentiation of a cell according to claim 3, wherein the probe comprises a detectable labeling substance.

5. A cell separation method comprising:
   a step of contacting a test cell with a probe comprising a protein (A) or (B) below and
   a step of separating a cell binding to the probe and a cell not binding thereto:
   (A) a protein comprising an amino acid sequence shown in SEQ ID NO: 1 and recognizing a sugar chain structure of "Fucα1-2Galβ1-3GlcNAc" and/or "Fucα1-2Galβ1-3GlcNAc;" and
   (B) a protein comprising an amino acid sequence in which one or two amino acids in the amino acid sequence shown in SEQ ID NO: 1 are deleted, substituted, inserted, or added, and recognizing a sugar chain structure of "Fucα1-2Galβ1-3GlcNAc" and/or "Fucα1-2Galβ1-3GalNAc;"
   wherein the cell binding to the probe indicates an undifferentiated state and
   wherein the cell not binding thereto indicates a differentiated state.

6. The cell separation method according to claim 5, wherein the probe comprises an optically detectable label, and wherein the separation of the cell binding to the probe and the cell not binding thereto is performed using a flow cytometer equipped with a cell sorter.

7. The cell separation method according to claim 5, wherein the probe comprises a magnetically detectable label, and wherein the separation of the cell binding to the probe and the cell not binding thereto is performed using a magnetic cell separation apparatus.

8. A method for producing an induced pluripotent stem cell, comprising:
   a step of subjecting a somatic cell to a pluripotency induction treatment,
   a step of contacting the pluripotency-induced cell with a probe comprising a protein (A) or (B) below, and
   a step of isolating a cell binding to the probe:
   (A) a protein comprising an amino acid sequence shown in SEQ ID NO: 1 and recognizing a sugar chain structure of "Fucα1-2Galβ1-3GlcNAc" and/or "Fucα1-2Galβ1-3GlcNAc;" and
   (B) a protein comprising an amino acid sequence in which one or two amino acids in the amino acid sequence shown in SEQ ID NO: 1 are deleted, substituted, inserted, or added, and recognizing a sugar chain structure of "Fucα1-2Galβ1-3GlcNAc" and/or "Fucα1-2Galβ1-3GalNAc;"
   wherein the cell binding to the probe indicates an undifferentiated state.

9. A method for producing a differentiated cell, comprising:
   a step of subjecting a stem cell to a differentiation induction treatment,
   a step of contacting the differentiation-induced cell with a probe comprising a protein (A) or (B) below, and
   a step of isolating a cell not binding to the probe:
   (A) a protein comprising an amino acid sequence shown in SEQ ID NO: 1 and recognizing a sugar chain structure of "Fucα1-2Galβ1-3GlcNAc" and/or "Fucα1-2Galβ1-3GlcNAc;" and
   (B) a protein comprising an amino acid sequence in which one or two amino acids in the amino acid sequence shown in SEQ ID NO: 1 are deleted, substituted, inserted, or added, and recognizing a sugar chain structure of "Fucα1-2Galβ1-3GlcNAc" and/or "Fucα1-2Galβ1-3GalNAc;"
   wherein the cell not binding to the probe indicates a differentiated state.

10. The method for determining differentiation of a cell according to claim 2, wherein the probe comprises a detectable labeling substance.

11. The method for determining differentiation of a cell according to claim 1, wherein the probe comprises a detectable labeling substance.

12. The method for determining differentiation of a cell according to claim 1, wherein the probe comprises the protein (A).

13. The method for determining differentiation of a cell according to claim 1, wherein the probe comprises the protein (B) comprising an amino acid sequence in which one amino acid in the amino acid sequence shown in SEQ ID NO: 1 is deleted, substituted, inserted, or added, and recognizing a sugar chain structure of "Fucα1-2Galβ1-3GlcNAc" and/or "Fucα1-2Galβ1-3GalNAc.

14. The method for determining differentiation of a cell according to claim 1, wherein the probe comprises the protein (B) comprising an amino acid sequence in which two amino acids in the amino acid sequence shown in SEQ ID NO: 1 are deleted, substituted, inserted, or added, and recognizing a sugar chain structure of "Fucα1-2Galβ1-3GlcNAc" and/or "Fucα1-2Galβ1-3GlcNAc.

15. The method for determining differentiation of a cell according to claim 12, wherein the test cell is an undifferentiated stem cell or a stem cell subjected to a differentiation induction treatment.

16. The method for determining differentiation of a cell according to claim 13, wherein the test cell is an undifferentiated stem cell or a stem cell subjected to a differentiation induction treatment.

17. The method for determining differentiation of a cell according to claim 14, wherein the test cell is an undifferentiated stem cell or a stem cell subjected to a differentiation induction treatment.

18. The method for determining differentiation of a cell according to claim 12, wherein the probe comprises a detectable labeling substance.

19. The method for determining differentiation of a cell according to claim 13, wherein the probe comprises a detectable labeling substance.

20. The method for determining differentiation of a cell according to claim 14, wherein the probe comprises a detectable labeling substance.

* * * * *

UNITED STATES PATENT AND TRADEMARK OFFICE
CERTIFICATE OF CORRECTION

PATENT NO. : 9,279,809 B2  
APPLICATION NO. : 14/381116  
DATED : March 8, 2016  
INVENTOR(S) : Tateno et al.

Page 1 of 1

It is certified that error appears in the above-identified patent and that said Letters Patent is hereby corrected as shown below:

In the Claims

Column 31, line 25, the text "3GlcNAc;" should read --3GalNAc;--

Column 31, line 54, the text "3GlcNAc;" should read --3GalNAc;--

Column 32, line 34, the text "3GlcNAc;" should read --3GalNAc;--

Column 32, line 53, the text "3GlcNAc;" should read --3GalNAc;--

Column 33, line 17, the text "3GlcNAc;" should read --3GalNAc;--

Signed and Sealed this  
Twenty-first Day of June, 2016

Michelle K. Lee  
*Director of the United States Patent and Trademark Office*

SEQUENCE LISTING

```
<160> NUMBER OF SEQ ID NOS: 1

<210> SEQ ID NO 1
<211> LENGTH: 156
<212> TYPE: PRT
<213> ORGANISM: Burkholderia cepacia

<400> SEQUENCE: 1

Met Pro Leu Leu Ser Ala Ser Ile Val Ser Ala Pro Val Val Thr Ser
1               5                   10                  15

Glu Thr Tyr Val Asp Ile Pro Gly Leu Tyr Leu Asp Val Ala Lys Ala
            20                  25                  30

Gly Ile Arg Asp Gly Lys Leu Gln Val Ile Leu Asn Val Pro Thr Pro
        35                  40                  45

Tyr Ala Thr Gly Asn Asn Phe Pro Gly Ile Tyr Phe Ala Ile Ala Thr
    50                  55                  60

Asn Gln Gly Val Val Ala Asp Gly Cys Phe Thr Tyr Ser Ser Lys Val
65                  70                  75                  80

Pro Glu Ser Thr Gly Arg Met Pro Phe Thr Leu Val Ala Thr Ile Asp
                85                  90                  95
```

```
Val Gly Ser Gly Val Thr Phe Val Lys Gly Gln Trp Lys Ser Val Arg
            100                 105                 110

Gly Ser Ala Met His Ile Asp Ser Tyr Ala Ser Leu Ser Ala Ile Trp
            115                 120                 125

Gly Thr Ala Ala Pro Ser Ser Gln Gly Ser Gly Asn Gln Gly Ala Glu
            130                 135                 140

Thr Gly Gly Thr Gly Ala Gly Asn Ile Gly Gly Gly
145                 150                 155
```